US011725174B2

(12) United States Patent
Nakai et al.

(10) Patent No.: US 11,725,174 B2
(45) Date of Patent: Aug. 15, 2023

(54) CELL CULTURE APPARATUS AND CELL CULTURE METHOD

(71) Applicant: FUJIFILM CORPORATION, Tokyo (JP)

(72) Inventors: Shinichi Nakai, Kanagawa (JP); Yoichi Nagai, Kanagawa (JP); Nobuyuki Haraguchi, Kanagawa (JP); Shigehisa Sugiyama, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 970 days.

(21) Appl. No.: 16/460,983

(22) Filed: Jul. 2, 2019

(65) Prior Publication Data

US 2019/0322975 A1 Oct. 24, 2019

Related U.S. Application Data

(63) Continuation of application No. PCT/JP2018/008175, filed on Mar. 2, 2018.

(30) Foreign Application Priority Data

Mar. 3, 2017 (JP) ................................ 2017-040956

(51) Int. Cl.
*B01D 61/14* (2006.01)
*B01D 61/18* (2006.01)
(Continued)

(52) U.S. Cl.
CPC ........... *C12M 29/04* (2013.01); *B01D 61/145* (2013.01); *B01D 61/146* (2022.08);
(Continued)

(58) Field of Classification Search
CPC ....... B01D 1/145; C12M 29/04; C12M 29/10; C12M 29/18
See application file for complete search history.

(56) References Cited

U.S. PATENT DOCUMENTS 4,420,398 A 12/1983 Franco
5,166,067 A 11/1992 Ishida et al.
(Continued)

FOREIGN PATENT DOCUMENTS

CN 1778887 A 5/2006
CN 1833090 A 9/2006
(Continued)

OTHER PUBLICATIONS

Lenntech MWCO tables—https://www.lenntech.com/services/mwco.htm—accessed Oct. 4, 2022 (Year: 2022).*
(Continued)

*Primary Examiner* — Bradley R Spies
(74) *Attorney, Agent, or Firm* — Solaris Intellectual Property Group, PLLC

(57) ABSTRACT

Provided is a cell culture apparatus including a culture vessel that stores a cell suspension containing cells; a first filter part that has a first filter membrane that performs membrane separation treatment on the cell suspension extracted from the culture vessel; a first circulation flow path that allows components blocked by the first filter membrane to return to the culture vessel; a second filter part that has a second filter membrane that performs membrane separation treatment on components of the cell suspension permeated through the first filter membrane; a second circulation flow path that allows components permeated through the second filter membrane to return to the culture vessel; and a recovery flow path that recovers components blocked by the second filter membrane. In the cell culture apparatus, an average hole diameter of the first filter membrane is 20 μm or smaller, and $0<B/A\leq 0.5$ is satisfied in a case where an average hole diameter of the first filter membrane is A and an average hole diameter of the second filter membrane is B; or an average hole diameter of the first filter membrane is 20
(Continued)

μm or smaller, and the second filter membrane is an ultrafiltration membrane.

14 Claims, 8 Drawing Sheets

(51) Int. Cl.

| | |
|---|---|
| ***C12M 1/00*** | (2006.01) |
| ***C12M 1/12*** | (2006.01) |
| ***C12M 1/26*** | (2006.01) |
| ***B01D 61/58*** | (2006.01) |
| ***C12N 5/00*** | (2006.01) |

(52) U.S. Cl.
CPC ........... *B01D 61/147* (2013.01); *B01D 61/18* (2013.01); *B01D 61/58* (2013.01); *C12M 29/10* (2013.01); *C12M 29/18* (2013.01); *C12M 33/14* (2013.01); *C12M 37/02* (2013.01); *C12M 39/00* (2013.01); *C12M 47/02* (2013.01); *C12N 5/0081* (2013.01); *B01D 2311/25* (2013.01); *B01D 2311/2688* (2013.01); *B01D 2315/08* (2013.01); *B01D 2315/10* (2013.01); *B01D 2317/025* (2013.01)

(56) References Cited

U.S. PATENT DOCUMENTS

| | | | | |
|---|---|---|---|---|
| 5,503,750 | A | 4/1996 | Russo, Jr. et al. | |
| 5,849,188 | A | 12/1998 | Arild et al. | |
| 2002/0055166 | A1 | 5/2002 | Cannon et al. | |
| 2002/0146817 | A1 | 10/2002 | Cannon et al. | |
| 2005/0186671 | A1 | 8/2005 | Cannon et al. | |
| 2006/0137883 | A1 | 6/2006 | Kluger et al. | |
| 2008/0032398 | A1 | 2/2008 | Cannon et al. | |
| 2008/0269468 | A1 | 10/2008 | Vogel et al. | |
| 2010/0075413 | A1* | 3/2010 | Zijlstra .................... | C07K 1/22 435/366 |
| 2012/0088282 | A1 | 4/2012 | Gaddy et al. | |
| 2015/0337343 | A1 | 11/2015 | Benkwitz et al. | |
| 2017/0306279 | A1 | 10/2017 | Kagawa et al. | |

FOREIGN PATENT DOCUMENTS

| | | | |
|---|---|---|---|
| CN | 200988816 | Y | 12/2007 |
| CN | 101215583 | A | 7/2008 |
| CN | 101490239 | A | 7/2009 |
| CN | 101503707 | A | 8/2009 |
| CN | 101586074 | A | 11/2009 |
| CN | 102311912 | A | 1/2012 |
| CN | 104995306 | A | 10/2015 |
| EP | 2041259 | A1 | 4/2009 |
| EP | 2330209 | A1 | 6/2011 |
| EP | 3591030 | A1 | 1/2020 |
| JP | H02-150272 | A | 6/1990 |
| JP | 2004-510431 | A | 4/2004 |
| JP | 2008-514237 | A | 5/2008 |
| JP | 2008-245537 | A | 10/2008 |
| JP | 2010-29109 | A | 2/2010 |
| JP | 2011-211961 | A | 10/2011 |
| JP | 2015-53892 | A | 3/2015 |
| TW | 2016-17289 | A | 5/2016 |
| WO | 83/00444 | A1 | 2/1983 |
| WO | 2016/117615 | A1 | 7/2016 |

OTHER PUBLICATIONS

"Principles of Food Engineering", ISBN 978-7-5019-9120-4, Mar. 31, 2013.
"Research of new technologies of continuous cycle of L-lactic acid fermentation", Nov. 15, 2011.
Zhou Yu-Ping et al. "A Review on Models of Microorganism Continuous Fermentation and Its Application" Institute of Microbiology, CAS, vol. 37, No. 2, China Academic Journal Electronic Publishing House. Feb. 20, 2010, p. 269-273.
English language translation of the following: Office action dated Apr. 2, 2022 from the SIPO in a Chinese patent application No. 201880010607.4 corresponding to the instant patent application. This office action translation is submitted now in order to supplement the understanding of the cited references which are being disclosed in the instant Information Disclosure Statement.
International Search Report issued in International Application No. PCT/JP2018/008175 dated May 29, 2018.
Written Opinion of the ISA issued in International Application No. PCT/JP2018/008175 dated May 29, 2018.
Extended European Search Report dated Feb. 21, 2020, issued in corresponding EP Patent Application No. 18760265.1.
Anonymous, "ESF 100G/200 G External Spin Filter for cell culture", Jan. 1, 2001, XP055668324, Retrieved from the Internet: URL:http://www.sart.corn.ua/ PDF/ biostat_esf 100g_en.pdf.
Myers, Michele M. et al., "Addressing Changes Associated with Technology Transfer: A Case Study", Current Trends in Monoclonal Antibody Development and Manufacturing, Jan. 1, 2010, X P055668335, pp. i-iii, 75-78.
English language translation of the following: Notification of Decision of Refusal dated Sep. 14, 2022 from the SIPO in a Chinese patent application No. 201880010607.4 corresponding to the instant patent application.
English language translation of the following: Office action dated May 15, 2023, from the SIPO in a Chinese patent application No. 201880010607.4 corresponding to the instant patent application.

* cited by examiner

100
CELL BREEDING SOLUTION
TO PURIFICATION STEP
FRESH MEDIUM
P1
P2
P3
P4
V1
V2
V3
V4
10
11
20
20a
20b
20c
21
22
23
24
30
30a
30c
31
32
33
34
40
51
52
53
54
55
56
57
58
59

100A
FRESH MEDIUM
CELL BREEDING SOLUTION
TO PURIFICATION STEP
P1
P2
P4
P5
P6
10
11
20
20a
20b
20c
21
22
23
24
30
30a
30b
30c
31
32
33
34
41
51
52
53A
53B
54
56
57
58
59

100B
TO PURIFICATION STEP
CELL BREEDING SOLUTION
FRESH MEDIUM
P1
P2
P4
P6
10
11
20
20a
20b
20c
21
22
23
24
30
30a
30b
30c
31
32
33
34
51
52
53
54
56
58
59

FIG. 6A

| EXAMPLE | CELL | | FILTRATION | FIRST FILTRATION | | | | | | | | SECOND FILTRATION | | | | | | | | FILTRATION CONDITION | | | CULTURE SOLUTION | | |
|---|---|---|---|---|---|---|---|---|---|---|---|---|---|---|---|---|---|---|---|---|---|---|---|---|---|
| | TYPE | AVERAGE VALUE OF CELL DIAMETER [μm] | RATIO OF HOLE DIAMETER B/A [-] | AVERAGE HOLE DIAMETER A [μm] | TYPE OF FILTRATION MEMBRANE | MESH WEFT x WARP [-] | YARN DIAMETER WEFT / WARP [μm] | FILTRATION METHOD | PERMEATION RATE OF CELLS [%] | PERMEATION RATE OF FINE PARTICLES OF 2 TO 4 μm [%] | PERMEATION RATE OF ANTIBODIES [%] | AVERAGE HOLE DIAMETER B [μm] | MOLECULAR WEIGHT CUT-OFF [kDa] | TYPE OF FILTRATION MEMBRANE | FILTRATION METHOD | RECOVERY METHOD | CONCENTRATION OF FINE PARTICLES OF 2 TO 4 μm IN PERMEATED LIQUID $10^7$ [PARTICLES/ml] | CONCENTRATION OF ANTIBODIES IN PERMEATED LIQUID [g/L] | CONCENTRATION OF ANTIBODIES IN RECOVERY SOLUTION [g/L] | PERFUSION RATIO X [-] | CIRCULATION RATIO Y [-] | Y/X [-] | CONCENTRATION OF CELLS IN CULTURE SOLUTION $10^7$ [cells/ml] | CONCENTRATION OF FINE PARTICLES OF 2 TO 4 μm $10^7$ [PARTICLES/ml] | CONCENTRATION OF ANTIBODIES [g/L] |
| EXAMPLE 1 | CHO CELL | 14 | 0.0004 | 6 | TWILL WOVEN METAL MESH | 500 x 3500 | 25/15 | TFF | 1 | 85 | 97 | 0.0025 | 3 | HOLLOW FIBER UF MEMBRANE | DEAD-END FILTRATION | BACKWASH RECOVERY | 0.001 | 0.01 | 2.4 | 0.5 | 4.5 | 9 | 12 | 1 | 0.3 |
| EXAMPLE 2 | CHO CELL | 14 | 0.0333 | 6 | TWILL WOVEN METAL MESH | 500 x 3500 | 25/15 | TFF | 1 | 84 | 96 | 0.2 | - | HOLLOW FIBER MF MEMBRANE | DEAD-END FILTRATION | BACKWASH RECOVERY | 0.013 | 2.3 | 2.3 | 0.5 | 4.5 | 9 | 11 | 1.3 | 2.3 |
| EXAMPLE 3 | CHO CELL | 14 | 0.1250 | 4 | TWILL WOVEN METAL MESH | 635 x 4300 | 20/13 | TFF | 0.5 | 60 | 95 | 0.5 | - | HOLLOW FIBER MF MEMBRANE | DEAD-END FILTRATION | BACKWASH RECOVERY | 0.33 | 2.1 | 2.1 | 0.5 | 4.5 | 9 | 7.9 | 7 | 2.1 |
| EXAMPLE 4 | CHO CELL | 14 | 0.0003 | 10 | TWILL WOVEN METAL MESH | 350 x 2600 | 30/22 | TFF | 14 | 97 | 99 | 0.0025 | 3 | HOLLOW FIBER UF MEMBRANE | DEAD-END FILTRATION | BACKWASH RECOVERY | 0.001 | 0.01 | 0.9 | 0.5 | 4.5 | 9 | 5.2 | 0.7 | 0.1 |
| EXAMPLE 5 | CHO CELL | 14 | 0.0125 | 0.2 | HOLLOW FIBER MF MEMBRANE | - | - | TFF | 0.01 | 1 | 88 | 0.0025 | 3 | HOLLOW FIBER UF MEMBRANE | DEAD-END FILTRATION | BACKWASH RECOVERY | 0.001 | 0.01 | 1.9 | 0.5 | 4.5 | 9 | 7.8 | 17 | 0.2 |
| EXAMPLE 6 | CHO CELL | 14 | 0.0025 | 1 | HOLLOW FIBER MF MEMBRANE | - | - | TFF | 1 | 3 | 90 | 0.0025 | 3 | HOLLOW FIBER UF MEMBRANE | DEAD-END FILTRATION | BACKWASH RECOVERY | 0.001 | 0.01 | 1.4 | 0.5 | 4.5 | 9 | 7 | 14 | 0.2 |
| EXAMPLE 7 | CHO CELL | 14 | 0.0175 | 0.2 | HOLLOW FIBER MF MEMBRANE | - | - | TFF | 0.01 | 1 | 88 | 0.0035 | 10 | HOLLOW FIBER UF MEMBRANE | DEAD-END FILTRATION | BACKWASH RECOVERY | 0.001 | 0.04 | 1.7 | 0.5 | 4.5 | 9 | 7.8 | 17 | 0.4 |
| EXAMPLE 8 | CHO CELL | 14 | 0.0300 | 0.2 | HOLLOW FIBER MF MEMBRANE | - | - | TFF | 0.01 | 1 | 88 | 0.0060 | 50 | HOLLOW FIBER UF MEMBRANE | DEAD-END FILTRATION | BACKWASH RECOVERY | 0.001 | 0.05 | 1.7 | 0.5 | 4.5 | 9 | 7.9 | 9 | 0.4 |
| EXAMPLE 8-2 | CHO CELL | 14 | 0.0350 | 0.2 | HOLLOW FIBER MF MEMBRANE | - | - | TFF | 0.01 | 1 | 88 | 0.0070 | 70 | HOLLOW FIBER UF MEMBRANE | DEAD-END FILTRATION | BACKWASH RECOVERY | 0.001 | 0.1 | 1.6 | 0.5 | 4.5 | 9 | 9.5 | 10 | 0.4 |
| EXAMPLE 9 | CHO CELL | 14 | 0.0420 | 0.2 | HOLLOW FIBER MF MEMBRANE | - | - | TFF | 0.01 | 1 | 88 | 0.0084 | 110 | HOLLOW FIBER UF MEMBRANE | DEAD-END FILTRATION | BACKWASH RECOVERY | 0.001 | 0.7 | 1.4 | 0.5 | 4.5 | 9 | 7.1 | 14 | 1.1 |
| EXAMPLE 10 | CHO CELL | 14 | 0.4000 | 0.2 | HOLLOW FIBER MF MEMBRANE | - | - | TFF | 0.01 | 1 | 88 | 0.08 | - | HOLLOW FIBER MF MEMBRANE | DEAD-END FILTRATION | BACKWASH RECOVERY | 0.08 | 1 | 1.5 | 0.5 | 4.5 | 9 | 7 | 14 | 1.6 |
| EXAMPLE 11 | CHO CELL | 14 | 0.0004 | 6 | TWILL WOVEN METAL MESH | 500 x 3500 | 25/15 | TFF | 1 | 85 | 97 | 0.0025 | 3 | HOLLOW FIBER UF MEMBRANE | DEAD-END FILTRATION | BACKWASH RECOVERY | 0.001 | 0.01 | 1.2 | 1.1 | 4.5 | 4.1 | 12 | 1 | 0.3 |
| EXAMPLE 12 | CHO CELL | 14 | 0.0004 | 6 | TWILL WOVEN METAL MESH | 500 x 3500 | 25/15 | TFF | 1 | 85 | 97 | 0.0025 | 3 | HOLLOW FIBER UF MEMBRANE | DEAD-END FILTRATION | BACKWASH RECOVERY | 0.001 | 0.01 | 0.6 | 1.9 | 4.5 | 2.4 | 12 | 1 | 0.3 |
| EXAMPLE 13 | CHO CELL | 14 | 0.0004 | 6 | TWILL WOVEN METAL MESH | 500 x 3500 | 25/15 | TFF | 1 | 85 | 97 | 0.0025 | 3 | HOLLOW FIBER UF MEMBRANE | DEAD-END FILTRATION | BACKWASH RECOVERY | 0.001 | 0.01 | 5 | 0.15 | 4.5 | 30 | 6 | 1 | 0.2 |
| EXAMPLE 14 | CHO CELL | 14 | 0.0004 | 6 | TWILL WOVEN METAL MESH | 500 x 3500 | 25/15 | TFF | 1 | 85 | 97 | 0.0025 | 3 | HOLLOW FIBER UF MEMBRANE | DEAD-END FILTRATION | BACKWASH RECOVERY | 0.001 | 0.01 | 2.4 | 0.09 | 4.5 | 50 | 6 | 1 | 0.05 |
| EXAMPLE 15 | CHO CELL | 14 | 0.0004 | 6 | TWILL WOVEN METAL MESH | 500 x 3500 | 25/15 | TFF | 1 | 85 | 97 | 0.0025 | 3 | HOLLOW FIBER UF MEMBRANE | DEAD-END FILTRATION | BACKWASH RECOVERY | 0.001 | 0.01 | 0.9 | 0.5 | 0.8 | 1.6 | 4.5 | 21 | 1.1 |
| EXAMPLE 16 | CHO CELL | 14 | 0.0004 | 6 | TWILL WOVEN METAL MESH | 500 x 3500 | 25/15 | TFF | 1 | 85 | 97 | 0.0025 | 3 | HOLLOW FIBER UF MEMBRANE | DEAD-END FILTRATION | BACKWASH RECOVERY | 0.001 | 0.01 | 1.9 | 0.5 | 9 | 18 | 7.7 | 0.6 | 0.1 |
| EXAMPLE 17 | CHO CELL | 14 | 0.0004 | 6 | TWILL WOVEN METAL MESH | 500 x 3500 | 25/15 | TFF | 1 | 85 | 97 | 0.0025 | 3 | HOLLOW FIBER UF MEMBRANE | DEAD-END FILTRATION | BACKWASH RECOVERY | 0.001 | 0.01 | 1.8 | 0.5 | 15 | 30 | 7.8 | 0.6 | 0.1 |
| EXAMPLE 18 | CHO CELL | 14 | 0.0004 | 6 | TWILL WOVEN METAL MESH | 500 x 3500 | 25/15 | TFF | 1 | 85 | 97 | 0.0025 | 3 | HOLLOW FIBER UF MEMBRANE | DEAD-END FILTRATION | BACKWASH RECOVERY | 0.001 | 0.01 | 2 | 0.09 | 0.18 | 2 | 2.7 | 30 | 1.1 |
| EXAMPLE 19 | CHO CELL | 14 | 0.0004 | 6 | TWILL WOVEN METAL MESH | 500 x 3500 | 25/15 | TFF | 1 | 85 | 97 | 0.0025 | 3 | HOLLOW FIBER UF MEMBRANE | DEAD-END FILTRATION | BACKWASH RECOVERY | 0.001 | 0.01 | 0.9 | 0.5 | 0.7 | 1.4 | 3 | 29 | 1.2 |
| EXAMPLE 20 | BHK CELL | 16 | 0.0004 | 6 | TWILL WOVEN METAL MESH | 500 x 3500 | 25/15 | TFF | 1 | 85 | 97 | 0.0025 | 3 | HOLLOW FIBER UF MEMBRANE | DEAD-END FILTRATION | BACKWASH RECOVERY | 0.001 | 0.01 | 2 | 0.5 | 4.5 | 9 | 7.9 | 0.9 | 0.2 |
| EXAMPLE 21 | CHO CELL | 14 | 0.0004 | 6 | TWILL WOVEN METAL MESH | 500 x 3500 | 25/15 | TFF | 1 | 85 | 97 | 0.0025 | 3 | HOLLOW FIBER UF MEMBRANE | TFF | CONTINUOUS RECOVERY | 0.001 | 0.01 | 2.8 | 0.5 | 4.5 | 9 | 13 | 1 | 0.3 |
| COMPARATIVE EXAMPLE 1 | CHO CELL | 14 | 0.6667 | 6 | TWILL WOVEN METAL MESH | 500 x 3500 | 25/15 | TFF | 1 | 85 | 97 | 4 | - | TWILL WOVEN METAL MESH | DEAD-END FILTRATION | BACKWASH RECOVERY | 26 | 0.4 | 0.4 | 0.5 | 4.5 | 9 | 1.9 | 42 | 0.4 |
| COMPARATIVE EXAMPLE 2 | CHO CELL | 14 | 0.5263 | 0.38 | HOLLOW FIBER MF MEMBRANE | - | - | TFF | 1 | 2 | 90 | 0.2 | - | HOLLOW FIBER MF MEMBRANE | DEAD-END FILTRATION | BACKWASH RECOVERY | 0.01 | 0.4 | 0.4 | 0.5 | 4.5 | 9 | 1.8 | 41 | 0.4 |
| COMPARATIVE EXAMPLE 3 | CHO CELL | 14 | - | 0.2 | HOLLOW FIBER MF MEMBRANE | - | - | TFF | 1 | 1 | 90 | - | - | - | - | - | - | - | - | 0.5 | - | - | 1.7 | 40 | 0.4 |
| COMPARATIVE EXAMPLE 4 | CHO CELL | 14 | - | 0.2 | HOLLOW FIBER MF MEMBRANE | - | - | TFF | 1 | 1 | 90 | - | - | - | - | - | - | - | - | 4 | - | - | 7.7 | 18 | 0.3 |

FIG. 6B

| EXAMPLES | RECOVERY PERCENTAGE OF ANTIBODY [%] | MAIN PEAK BY SIZE EXCLUSION CHROMATOGRAPHY [%] | EVALUATION | | | | | | | | | |
|---|---|---|---|---|---|---|---|---|---|---|---|---|
| | | | CELL GROWTH PROPERTIES | AMOUNT OF MEDIUM USED | AGGREGATE IN CULTURE TANK | CONCENTRATION OF FINE PARTICLES IN CULTURE TANK | CONCENTRATION OF ANTIBODIES IN CULTURE TANK | FILTRATION CLOGGING OF FIRST STAGE | FILTRATION CLOGGING OF SECOND STAGE | RECOVERY PERCENTAGE OF ANTIBODY | MAIN PEAK PERCENTAGE (ANTIBODY QUALITY) | COMPREHENSIVE JUDGEMENT |
| EXAMPLES 1 | 97.8 | 99.2 | A | A | A | A | A | B | C | A | A | B |
| EXAMPLES 2 | 83.3 | 96.0 | A | A | C | A | C | B | A | B | C | B |
| EXAMPLES 3 | 83.3 | 95.3 | B | A | C | B | C | B | A | B | C | B |
| EXAMPLES 4 | 97.8 | 99.1 | B | A | A | A | A | C | C | A | A | B |
| EXAMPLES 5 | 97.8 | 99.1 | B | A | A | C | A | A | C | A | A | B |
| EXAMPLES 6 | 97.8 | 99.2 | B | A | A | C | A | A | C | A | A | B |
| EXAMPLES 7 | 95.5 | 99.1 | B | A | A | C | A | A | C | A | A | B |
| EXAMPLES 8 | 95.5 | 99.4 | B | A | A | B | A | A | C | A | A | B |
| EXAMPLES 8-2 | 95.2 | 99.5 | A | A | A | B | A | A | C | A | A | A |
| EXAMPLES 9 | 86.4 | 97.8 | B | A | B | C | B | A | C | B | B | B |
| EXAMPLES 10 | 82.4 | 95.4 | B | A | C | C | B | A | B | B | C | B |
| EXAMPLES 11 | 97.8 | 99.1 | A | B | A | A | A | B | C | A | A | B |
| EXAMPLES 12 | 97.8 | 99.0 | A | C | A | A | A | B | C | A | A | B |
| EXAMPLES 13 | 97.8 | 99.1 | B | A | A | A | A | B | C | A | A | B |
| EXAMPLES 14 | 97.8 | 99.0 | B | A | A | A | A | B | C | A | A | B |
| EXAMPLES 15 | 80.4 | 99.1 | C | A | B | C | B | B | C | B | A | C |
| EXAMPLES 16 | 98.9 | 99.0 | A | A | B | A | A | C | C | A | A | B |
| EXAMPLES 17 | 99.3 | 99.1 | A | A | B | A | A | C | C | A | A | B |
| EXAMPLES 18 | 62.1 | 99.1 | C | A | B | C | B | B | C | C | A | C |
| EXAMPLES 19 | 78.9 | 99.0 | C | A | B | C | B | B | C | C | A | C |
| EXAMPLES 20 | 97.8 | 99.1 | B | A | A | A | A | B | C | A | A | B |
| EXAMPLES 21 | 97.8 | 99.0 | A | A | A | A | A | B | C | A | A | A |
| COMPARATIVE EXAMPLE 1 | 83.3 | 95.6 | D | A | B | D | B | B | C | B | C | D |
| COMPARATIVE EXAMPLE 2 | 83.3 | 95.9 | D | A | B | D | B | B | B | B | C | D |
| COMPARATIVE EXAMPLE 3 | 81.8 | 94.0 | D | A | B | D | B | B | - | B | D | D |
| COMPARATIVE EXAMPLE 4 | 97.3 | 93.8 | B | D | A | C | A | A | - | A | D | D |

CELL CULTURE APPARATUS AND CELL CULTURE METHOD

CROSS-REFERENCE TO RELATED APPLICATIONS

This application is a continuation application of International Application No. PCT/JP2018/008175 filed Mar. 2, 2018, the disclosure of which is incorporated herein by reference in its entirety. Further, this application claims priority from Japanese Patent Application No. 2017-040956, filed Mar. 3, 2017, the disclosure of which is incorporated herein by reference in its entirety.

BACKGROUND OF THE INVENTION

1. Field of the Invention

The disclosed technology relates to a cell culture apparatus and a cell culture method.

2. Description of the Related Art

As techniques for separating specific components from a culture solution by membrane separation treatment, the following techniques are known.

For example, JP2010-029109A discloses a sampling device including a bioreactor; a sampling line which circulates a culture solution in the bioreactor; a filtration device of a cross-flow type filter which is provided in the middle of the sampling line to separate contaminating microorganisms in the culture solution; a recovery line which connects the bioreactor and a permeation side chamber of the filtration device; and a filtration membrane unit which is installed in the middle of the recovery line to capture the contaminating microorganisms.

JP2011-211961A discloses a filtration device including a stock solution tank which stores a liquid medium; a first filtration means of a cross-flow type which separates foreign substances in the liquid medium; and a second filtration means of a dead-end system which further filters the liquid medium that has been filtered by the first filtration means. This filtration device further includes a storage tank which stores the liquid medium filtered by the first filtration means; a pressure adjusting means which adjusts a pressure in the storage tank; and a pump which supplies the liquid medium stored in the storage tank to the second filtration means.

JP2015-053892A discloses a semicontinuous culture device including a culture tank which stores a culture solution and cultures bacteria in the culture solution; a spin filter which is disposed in the culture tank and separates bacterial bodies from the culture solution; and an ultrafiltration membrane device as a first filtration means which recovers a product produced by bacteria from the culture solution. The spin filter is connected to a culture solution conduit pipe that supplies the culture solution to the ultrafiltration membrane device, and the culture solution conduit pipe is connected to the ultrafiltration membrane device via a microfiltration membrane device which disposed on the way to the ultrafiltration membrane. The ultrafiltration membrane device includes a filtrate conduit pipe that circulates its filtrate in the culture tank, and the filtrate conduit pipe is connected to the culture tank via the microfiltration membrane device.

SUMMARY OF THE INVENTION

Perfusion culture is exemplified as a culture system of cells used for producing biopharmaceuticals obtained by utilizing an antibody secreted by cells.

Perfusion culture is a culture system in which a culture solution containing cells is continuously filtered and discharged, while a fresh medium containing nutrient components is continuously supplied to a culture tank.

In perfusion culture, unnecessary components for cell culture, such as dead cells, crushed cells, deoxyribonucleic acid (DNA), Host Cell Protein (HCP), antibodies, and waste products are discharged in large amounts. Therefore, cell growth is promoted, and antibody productivity is improved. However, an amount of medium used increases according to an increase in amount of unnecessary components discharged, and thus a production cost of antibodies increases.

The disclosed technology is made in view of the above-mentioned point, and an object thereof is to make it possible to improve antibody productivity while reducing an amount of medium used.

One embodiment of a cell culture apparatus according to the disclosed technology comprises a culture vessel that stores a cell suspension containing cells; a first filter part that has a first filter membrane that performs membrane separation treatment on the cell suspension extracted from the culture vessel; a first circulation flow path that allows components blocked by the first filter membrane to return to the culture vessel; a second filter part that has a second filter membrane that performs membrane separation treatment on components of the cell suspension permeated through the first filter membrane; a second circulation flow path that allows components permeated through the second filter membrane to return to the culture vessel; and a recovery flow path that recovers components blocked by the second filter membrane. In the cell culture apparatus according to the disclosed technology, an average hole diameter of the first filter membrane is 20 μm or smaller; and $0<B/A\leq 0.5$ is satisfied in a case where the average hole diameter of the first filter membrane is A, and an average hole diameter of the second filter membrane is B.

Another embodiment of a cell culture apparatus according to the disclosed technology comprises a culture vessel that stores a cell suspension containing cells; a first filter part that has a first filter membrane that performs membrane separation treatment on the cell suspension extracted from the culture vessel; a first circulation flow path that allows components blocked by the first filter membrane to return to the culture vessel; a second filter part that has a second filter membrane that performs membrane separation treatment on components of the cell suspension permeated through the first filter membrane; a second circulation flow path that allows components permeated through the second filter membrane to return to the culture vessel; and a recovery flow path that recovers components blocked by the second filter membrane, in which an average hole diameter of the first filter membrane is 20 μm or smaller, and the second filter membrane is an ultrafiltration membrane.

A system of the membrane separation treatment by the second filter membrane may be a dead-end system. In this case, the recovery flow path may be provided between the first filter part and the second filter part.

A system of the membrane separation treatment by the second filter membrane may be a tangential flow system. In this case, the recovery flow path may be connected to an outlet port of the second filter part by which components blocked by the second filter membrane flow outside the second filter part.

The cell culture apparatus according to the disclosed technology may further comprise a liquid sending part that generates a liquid flow from a permeation side to a supply side of the second filter part.

The average hole diameter of the second filter membrane is preferably larger than 0 μm and 1 μm or smaller.

The first filter membrane may have an inlet-side opening which is formed on a first surface, and an outlet-side opening which is formed on a second surface opposite to the first surface and is communicated with the inlet-side opening; and the inlet-side opening and the outlet-side opening may be disposed at positions mutually offset in a direction parallel to a membrane surface.

The first filter membrane may have an inlet-side opening which is formed on a first surface, and an outlet-side opening which is formed on a second surface opposite to the first surface and is communicated with the inlet-side opening; and a path connecting the inlet-side opening and the outlet-side opening may be non-linear.

The first filter membrane may be formed of a mesh formed by twill-weaving fibrous members. In this case, the mesh may be made of metal.

The first filter membrane may be a microfiltration membrane.

The second filter membrane may be a microfiltration membrane.

In addition, the second filter membrane may be an ultrafiltration membrane. In this case, a molecular weight cut-off of the second filter membrane is preferably more than 0 kDa and 100 kDa or less, and is more preferably 30 kDa to 70 kDa.

One embodiment of a cell culture method according to the disclosed technology comprises a first membrane separation step of using a first filter membrane to perform membrane separation treatment on a cell suspension extracted from a culture vessel that stores the cell suspension containing cells, and allowing components blocked by the first filter membrane to return to the culture vessel; a second membrane separation step of using a second filter membrane to perform membrane separation treatment on components permeated through the first filter membrane, and allowing components permeated through the second filter membrane to return to the culture vessel; and a recovery step of recovering components blocked by the second filter membrane via a recovery flow path. An average hole diameter of the first filter membrane is 20 μm or smaller. The first filter membrane and the second filter membrane are configured such that $0<B/A\geq 0.5$ is satisfied in a case where an average hole diameter of the first filter membrane is A, and an average hole diameter of the second filter membrane is B.

Another embodiment of a cell culture method according to the disclosed technology comprises a first membrane separation step of using a first filter membrane to perform membrane separation treatment on a cell suspension extracted from a culture vessel that stores the cell suspension containing cells, and allowing components blocked by the first filter membrane to return to the culture vessel; a second membrane separation step of using a second filter membrane to perform membrane separation treatment on components permeated through the first filter membrane, and allowing components permeated through the second filter membrane to return to the culture vessel; and a recovery step of recovering components blocked by the second filter membrane via a recovery flow path, in which an average hole diameter of the first filter membrane is 20 μm or smaller, and the second filter membrane is an ultrafiltration membrane.

A perfusion ratio and a circulation ratio are preferably determined such that $1.5\leq Y/X$ is satisfied in a case where a perfusion ratio, which is a ratio of an amount of components recovered in the recovery step per day to an amount of the cell suspension stored in the culture vessel, is X, and a circulation ratio, which is a ratio of an amount of components permeated through the first filter membrane in the first membrane separation step per day to the amount of the cell suspension stored in the culture vessel, is Y.

A perfusion ratio is preferably 0.1 to 2, and a circulation ratio is preferably 0.2 to 10.

A concentration of the cells contained in the cell suspension stored in the culture vessel is preferably $2\times10^7$ cells/ml or more, and a concentration of fine particles that have a particle diameter of 2 μm to 4 μm and are contained in the cell suspension stored in the culture vessel is preferably $40\times10^7$ particles/ml or less.

In the membrane separation treatment in the first membrane separation step, a permeation rate of the cells is preferably 20% or less, and a permeation rate of fine particles having a particle diameter of 2 μm to 4 μm is preferably 30% or more.

A concentration of fine particles that have a particle diameter of 2 μm to 4 μm and are contained in the components permeated through the second filter membrane is preferably $1\times10^7$ particles/ml or less.

In a case where the cell is a cell that expresses an antibody, a concentration of the cells contained in the cell suspension stored in the culture vessel is preferably $2\times10^7$ particles/ml or more, and a concentration of the antibodies contained in the cell suspension stored in the culture vessel is preferably 4 g/l or less.

In a case where the cell is a cell that expresses an antibody, a permeation rate of the antibodies is preferably 30% or more in the membrane separation treatment in the first membrane separation step.

In a case where the cell is a cell that expresses an antibody, a concentration of the antibodies contained in the components permeated through the second filter membrane is preferably 1 g/l or less.

In a case where the cell is a cell that expresses an antibody, a concentration of the antibodies contained in the components blocked by the second filter membrane is preferably 0.5 g/l or more.

A system of the membrane separation treatment by the first filter membrane may be a tangential flow system.

A system of the membrane separation treatment by the second filter membrane may be a tangential flow system.

A system of the membrane separation treatment by the second filter membrane may be a dead-end system.

In a case where a system of the membrane separation treatment by the second filter membrane is the dead-end system, the cell culture method according to the disclosed technology may further comprise a backwash step of sending the components blocked by the second filter membrane to the recovery flow path via a liquid flow from a permeation side to a supply side of a membrane surface of the second filter membrane.

In a case where a system of the membrane separation treatment by the second filter membrane is the tangential flow system, the components blocked by the second filter membrane may be continuously sent to the recovery flow path in the recovery step.

The cell may be a CHO cell.

According to the disclosed technology, it is possible to improve antibody productivity while reducing an amount of medium used.

BRIEF DESCRIPTION OF THE DRAWINGS

FIG. 6A is a table showing conditions when cells are cultured by using the cell culture apparatus according to the embodiment of the disclosed technology.

FIG. 6B is a table showing results of evaluation of a plurality of items after culturing cells by using the cell culture apparatus according to the embodiment of the disclosed technology.

DESCRIPTION OF THE PREFERRED EMBODIMENTS

Figure 1:
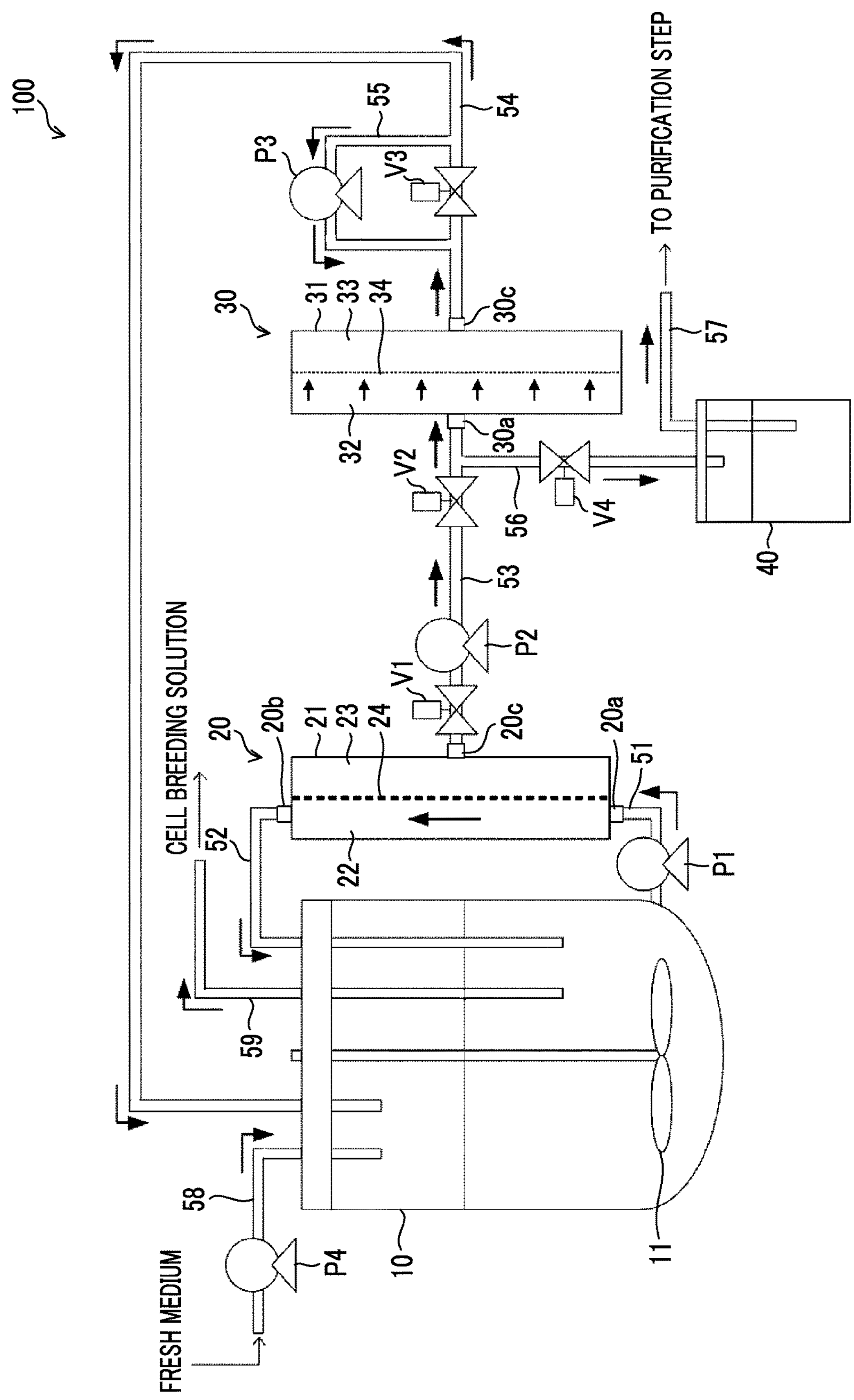
FIG. 1 is a view showing a configuration of a cell culture apparatus according to a first embodiment of the disclosed technology.

Hereinafter, an example of an embodiment of the disclosed technology will be described with reference to the drawings. In each of the drawings, the same or equivalent components and parts are denoted by the same reference numerals.

First Embodiment

FIG. 1 is a view showing a configuration of a cell culture apparatus 100 according to a first embodiment of the disclosed technology. The cell culture apparatus 100 can be suitably used in, for example, cell culture for expressing an antibody in animal cells.

Cells used for antibody expression are not particularly limited. Examples thereof include animal cells; plant cells; eukaryotic cells such as yeast; prokaryotic cells such as *Bacillus subtilis; E. coli*; and the like. Animal cells such as CHO cells, BHK-21 cells, and SP2/0-Ag14 cells are preferable, and CHO cells are more preferable.

Antibodies to be expressed in animal cells are not particularly limited. Examples thereof include an anti-IL-6 receptor antibody, an anti-IL-6 antibody, an anti-glypican-3 antibody, an anti-CD3 antibody, an anti-CD20 antibody, an anti-GPIIb/IIIa antibody, an anti-TNF antibody, an anti-CD25 antibody, an anti-EGFR antibody, an anti-Her2/neu antibody, an anti-RSV antibody, an anti-CD33 antibody, an anti-CD52 antibody, an anti-IgE antibody, an anti-CD11a antibody, an anti-VEGF antibody, and an anti-VLA4 antibody, and the like. Antibodies include not only monoclonal antibodies derived from animals such as humans, mice, rats, hamsters, rabbits, and monkeys but also artificially modified antibodies such as chimeric antibodies, humanized antibodies, and bispecific antibodies.

An obtained antibody or fragments thereof can be purified to have homogeneity. For separation and purification of the antibody or fragments thereof, separation and purification methods generally used in polypeptides may be used. It is possible to perform separation and purification of antibodies by appropriately selecting and combining, for example, chromatography columns such as affinity chromatography, filters, ultrafiltration, salting out, dialysis, SDS polyacrylamide gel electrophoresis and isoelectric focusing electrophoresis, and the like, but methods are not limited thereto. A concentration of the obtained antibodies can be measured by measurement of absorbance, or by enzyme-linked immunosorbent assay (ELISA) or the like.

The cell culture apparatus 100 includes a culture vessel 10 that stores a cell suspension containing cells; a first filter part 20 that has a first filter membrane 24 that performs membrane separation treatment on the cell suspension extracted from the culture vessel 10; and a flow path 52 as a first circulation flow path that allows components blocked by the first filter membrane 24 to return to the culture vessel 10. The cell culture apparatus 100 further includes a second filter part 30 that has a second filter membrane 34 that performs membrane separation treatment on components of the cell suspension permeated through the first filter membrane 24; a flow path 54 as a second circulation flow path that allows components permeated through the second filter membrane 34 to return to the culture vessel 10; and recovery flow paths 56 and 57 that recover components blocked by the second filter membrane 34.

The culture vessel 10 is a vessel that stores a medium and a cell suspension containing cells used for antibody expression. Inside the culture vessel 10, a stirring device having a stirring blade 11 is provided. By rotating the stirring blade 11, the medium stored together with the cells within the culture vessel 10 is stirred, and therefore homogeneity of the medium is maintained.

One end of the flow path 51 is connected to the bottom of the culture vessel 10, and the other end is connected to an inlet port 20*a* of the first filter part 20. In the middle of the flow path 51, a pump P1 that extracts the cell suspension stored in the culture vessel 10 and sends it to the first filter part 20 is provided.

The first filter part 20 includes a vessel 21; and the first filter membrane 24 that separates a space within the vessel 21 into a supply side 22 and a permeation side 23 and performs membrane separation treatment on the cell suspension extracted from the culture vessel 10. In addition, the first filter part 20 has, on the supply side 22, an inlet port 20*a* through which the cell suspension flows in, and an outlet port 20*b* through which the cell suspension flows out. The cell suspension extracted from the culture vessel 10 passes through the first filter membrane 24 while flowing into the vessel 21 from the inlet port 20*a* and flowing out of the vessel 21 from the outlet port 20*b*. The first filter part 20 performs the membrane separation treatment according to a tangential flow (cross flow) system in which permeated components are sent to a permeation side while allowing a liquid, which is a target of the membrane separation treatment, to flow along a membrane surface of the first filter membrane 24 (in a direction parallel to the membrane surface). A tangential flow system, which is a system of the membrane separation treatment by the first filter membrane 24, may form a flow in which the cell suspension extracted from the culture vessel circulates in a direction parallel to the membrane surface of the first filter membrane 24, or may form a flow in which the cell suspension alternately reciprocates in parallel along with the membrane surface of the first filter membrane 24. In a case of forming a circulating flow, for example, KrosFlo perfusion culture flow path device (KML-100, KPS-200, KPS-600) of Spectrum Laboratories, Inc. can be suitably used. In addition, in a case of forming alternately reciprocating flow, ATF system of REPLIGEN can be suitably used.

Relatively large-sized components contained in the cell suspension are not permeated through the first filter membrane 24, flow out from the outlet port 20*b* to the outside of the vessel 21, and return to the inside of the culture vessel 10 via the flow path 52. In other words, components blocked by the first filter membrane 24 among the cell suspension extracted from the culture vessel 10 return to the inside of the culture vessel 10 via the flow path 52. The flow path 52 is an example of the first circulation flow path in the disclosed technology. On the other hand, relatively small-sized components contained in the cell suspension are permeated through the first filter membrane 24, and are discharged from an exhaust port 20*c* provided on the permeation side 23 to the outside of the vessel 21. The flow path 53 provided with the pump P2 is connected to the permeation side 23 of the first filter part 20, and components discharged to the permeation side 23 are sent to the second filter part 30 via the flow path 53.

In the cell culture apparatus 100 according to the present embodiment, the first filter membrane 24 is used for the purpose of separating cells and unnecessary components for cell culture. Examples of unnecessary components for cell culture include dead cells, crushed cells, DNA, HCP, antibodies, waste products, and the like. In other words, the first filter membrane 24 has a separation performance suitable for allowing unnecessary components for cell culture such as dead cells, crushed cells, DNA, HCP, antibodies, and waste products to be permeated, while blocking permeation of cells. A size of cells cultured in the culture vessel 10 is assumed to be larger than 20 μm. In addition, a size of dead cells and crushed cells is assumed to be 1 μm to 10 μm. Furthermore, a size of DNA, HCP, and antibody is assumed to be about several tens of nm.

An average hole diameter of the first filter membrane 24 is preferably larger than 0 and 20 μm or smaller, is more preferably 0.05 μm to 10 μm, is even more preferably 0.1 μm to 9 μm, and is most preferably 2 μm to 8 μm. In a case where an average hole diameter of the first filter membrane 24 is 20 μm or smaller, the risk of cells being permeated through the first filter membrane 24 can be reduced, and a decrease in the number of cells in the culture vessel 10 can be reduced. In a case of using a mesh, an average hole diameter of the first filter membrane 24 can be measured at a separated particle diameter by 95%. In a case of using a microfiltration membrane or an ultrafiltration membrane, an average hole diameter of the first filter membrane 24 can be measured by a mercury intrusion method. An ultrafiltration membrane (referred to as an Ultrafiltration Membrane (UF membrane) in some cases) is a filtration membrane that has an average hole diameter of 0.001 to 0.01 μm, which is a smaller average hole diameter than that of a microfiltration membrane (referred to as a Microfiltration Membrane (MF membrane) in some cases), and in which a separation performance is defined by a molecular weight cut-off.

Figure 7:
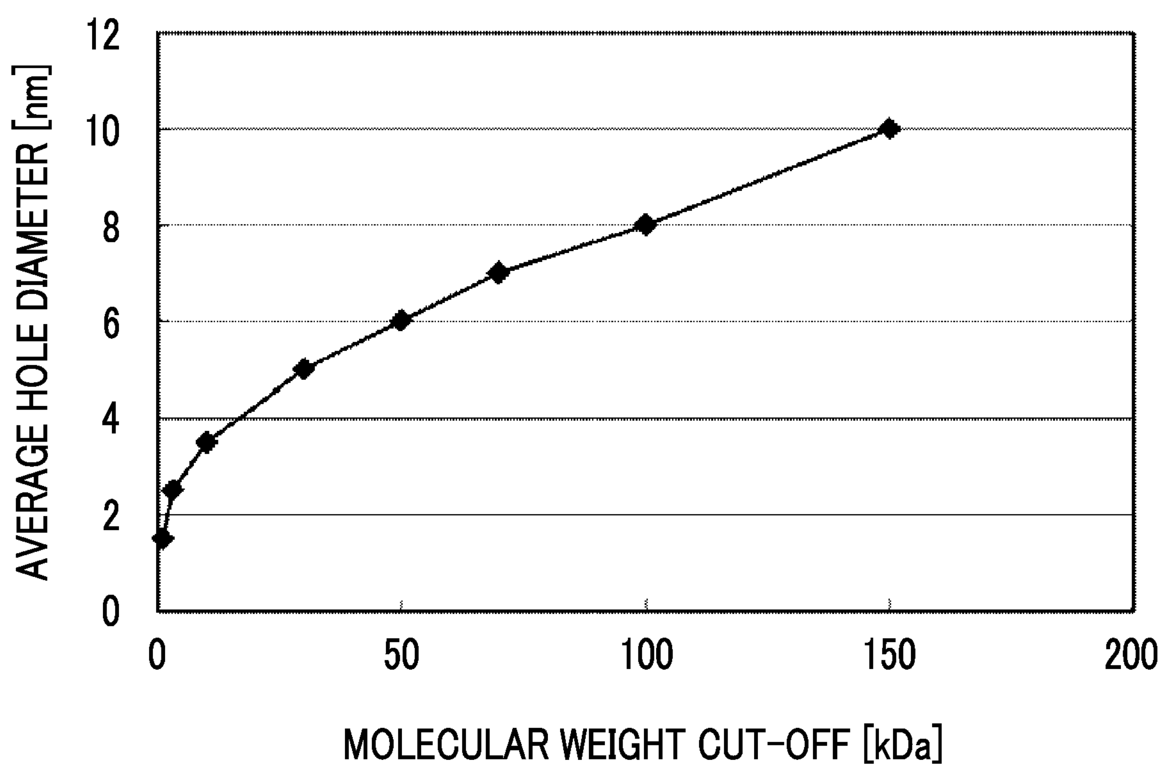
FIG. 7 is a graph showing a relationship between a molecular weight cut-off and an average hole diameter of an ultrafiltration membrane.

In an ultrafiltration membrane having a small hole diameter, it may be difficult to measure an average hole diameter by a mercury intrusion method. In this case, an average hole diameter of the ultrafiltration membrane can be estimated based on a molecular weight cut-off. Specifically, as described in http://chemeng.in.coocan.jp/memb/m_mb4.html, a molecular weight of a standard substance, which is obtained when a blocking percentage becomes 90% after permeating of a plural kinds of standard substances having known molecular weights through a target ultrafiltration membrane, is defined as a molecular weight cut-off of this ultrafiltration membrane. Because a molecular size can be estimated from a molecular weight of a standard substance, an average hole diameter of an ultrafiltration membrane can be estimated based on a molecular weight cut-off. Specifically, as described in Table 1, an average hole diameter is estimated from a molecular weight cut-off. In a case where a molecular weight cut-off does not match a molecular weight of a standard substance, an average hole diameter can be estimated by plotting a molecular weight cut-off and an average hole diameter and interpolating by linear interpolation or the like. As an example, FIG. 7 shows an example when a molecular weight cut-off and an average hole diameter of Table 1 are plotted and interpolated. Estimated values thus obtained can be used as an average hole diameter of an ultrafiltration membrane.

TABLE 1

| Molecular weight cut-off (kDa) | Estimated value of average hole diameter (nm) |
|---|---|
| 1 | 1.5 |
| 3 | 2.5 |
| 10 | 3.5 |
| 30 | 5 |
| 50 | 6 |
| 70 | 7 |
| 100 | 8 |
| 150 | 10 |

As the first filter membrane 24, it is possible to use a mesh filter configured by weaving fibrous members in a mesh shape. By using a mesh filter as the first filter membrane, it is possible to promote discharge of unnecessary components for cell culture including dead cells and crushed cells to a permeation side, compared to a case where a hollow fiber membrane is used. Accordingly, unnecessary components for cell culture can be effectively removed from the culture vessel 10, and growth of cells in the culture vessel 10 can be improved.

In addition, it is possible to use a hollow fiber membrane such as a microfiltration membrane and an ultrafiltration membrane as the first filter membrane 24. By using a hollow fiber membrane as the first filter membrane 24, the risk of cells being permeated to a permeation side can be reduced compared to a case of using a mesh filter. Furthermore, it is possible to reduce the risk of occurrence of clogging due to entry of cells into the first filter membrane 24. Accordingly, loss of cells can be reduced.

Figure 2:
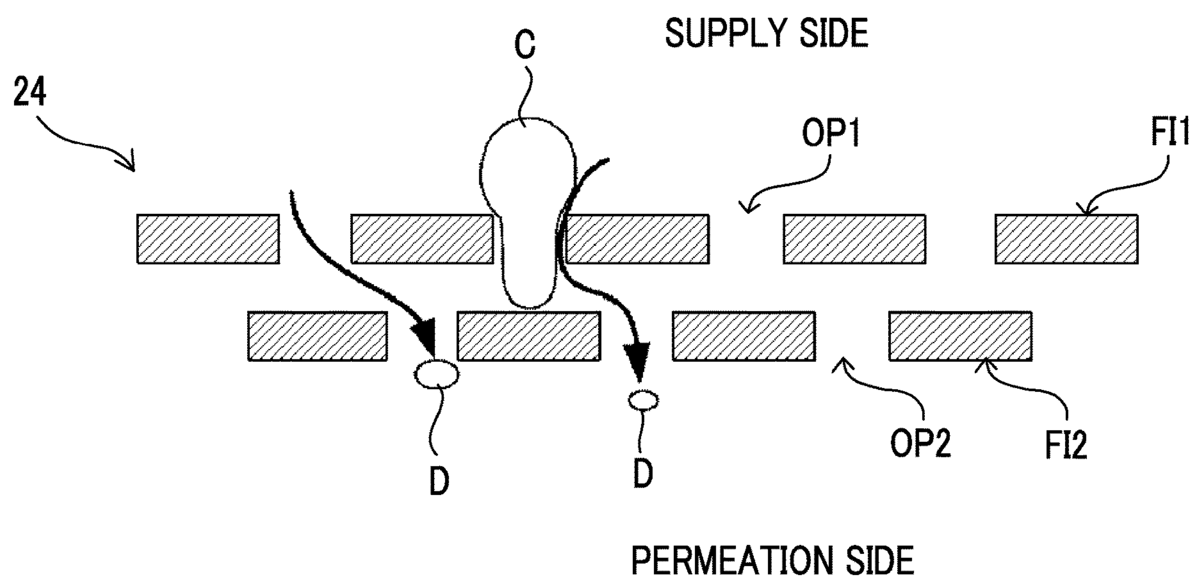
FIG. 2 is a cross-sectional view showing an example of a structure of a mesh filter used as a first filter membrane according to the embodiment of the disclosed technology.

FIG. 2 is a cross-sectional view showing an example of a structure of a mesh filter that can be used as the first filter membrane 24. A filter that can be used as the first filter membrane 24 is not limited to the filter shown in FIG. 2. FIG. 2 illustrates a case where a cell C and debris D are separated by using the first filter membrane 24. The debris D is an unnecessary component for cell culture, such as dead cells, crushed cells, deoxyribonucleic acids (DNA), host cell proteins (HCP), antibodies, and waste products.

The first filter membrane 24 has an inlet-side opening OP1 formed on a first surface FI1 on a supply side, and an outlet-side opening OP2 that is formed on a second surface FI2 on a permeation side and that is communicated with the opening OP1. The opening OP1 and the opening OP2 are disposed at positions mutually offset in the direction parallel to the membrane surface of the first filter membrane 24. In other words, a path connecting the opening OP1 and the opening OP2 is non-linear and is bent or curved. In the present embodiment, the opening OP1 and the opening OP2 have no portions overlapping to each other. In other words, the first filter membrane 24 does not have a see-through hole penetrating linearly between the first surface FI1 and the second surface FI2. The opening OP1 and the opening OP2 may partially overlap. The first filter membrane 24 is formed by interweaving fibrous members made of metal or plastic, for example.

By using the first filter membrane 24 having the above-described structure, the cells C flowing along the membrane surface of the first filter membrane 24 on the supply side of the first filter part 20 can be infiltrated into the inside of the first filter membrane 24 from the opening OP1 on the supply side. However, because the opening OP2 on the permeation side of the first filter membrane 24 is disposed at a position offset from the opening OP1 on the supply side, or because a path connecting the opening OP1 and the opening OP2 is nonlinear, the cells C infiltrated into the inside of the first filter membrane 24 cannot easily flow out to the permeation side compared to the debris D.

On the other hand, because the debris D is sufficiently smaller than a size of the cell C, it can easily flow out to the permeation side of the first filter membrane 24. In addition, the debris D can flow out to the permeation side through a flank of the cell C infiltrated into the opening OP1 of the first filter membrane 24.

For example, in a case where membrane separation treatment is performed by using a simple mesh-like filter membrane formed by plain-weaving fibrous members, cells easily flow out to a permeation side through a mesh of the filter membrane by being deformed. In a case where a mesh size of a filter membrane is reduced to prevent the outflow of cells to the permeation side, clogging occurs, or cells are divided due to the mesh of the filter membrane and thus flow out to the permeation side. As described above, in a case of using a filter membrane having a simple structure such as plain-weaved mesh in the membrane separation treatment, it is difficult to properly separate cells and debris in some cases even in a case where a size of a mesh of a filter membrane is appropriately selected.

On the other hand, according to the filter membrane having the structure shown in FIG. 2, because the opening OP2 on the permeation side of the first filter membrane 24 is disposed at a position offset from the opening OP1 on the supply side, or because a path connecting the opening OP1 and the opening OP2 is nonlinear, the outflow of the cells C infiltrated into the inside of the first filter membrane 24 to the permeation side is suppressed, and therefore the cell C and the debris D can be properly separated. In addition, because the cells C are unlikely to be infiltrated into a deep portion of the first filter membrane 24 in a thickness direction, blocking (clogging) of the filter membrane can be suppressed, and damage to cells can be reduced in the membrane separation treatment.

Figure 3A:
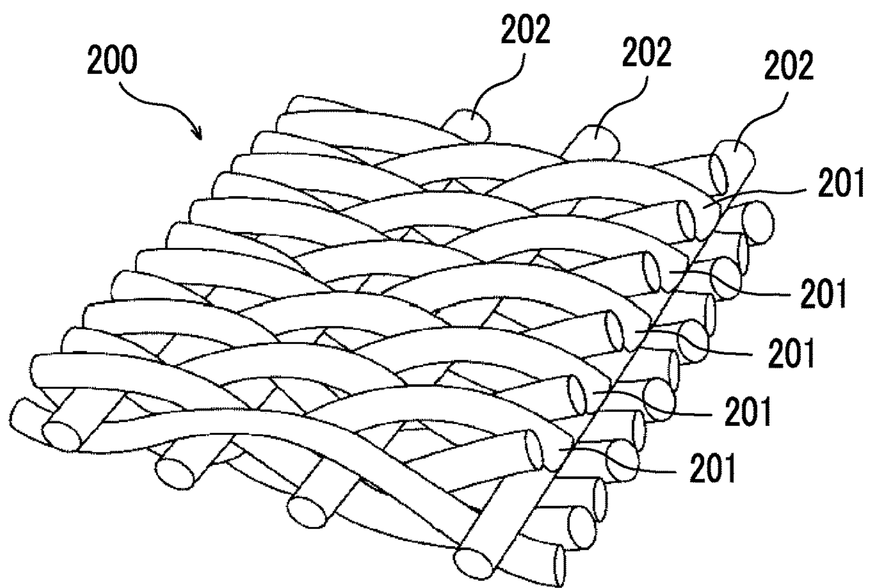
FIG. 3A is a perspective view showing a structure of a twill woven mesh that can be used as the first filter membrane according to the embodiment of the disclosed technology.

As the first filter membrane 24, it is possible to suitably use, for example, a twill woven mesh 200 formed by twill-weaving fibrous members as shown in FIG. 3A. The twill woven mesh 200 has a structure in which adjacent weft yarns 201 are intimately engaged with each other, and weft yarns 201 are woven so as to be entangled with the warp yarns 202 having a predetermined gap while the weft yarns 201 pass over the warp yarns 202 n by n. n is a natural number of 2 or more (n≥2). In the twill woven mesh 200, there is no see-through hole of a mesh, and an opening is formed by a gap formed at the intersection of the weft yarn 201 and the warp yarn 202. Fibrous members used for the twill woven mesh 200 are made of, for example, a metal such as stainless steel or a resin such as polyester, and a metal such as stainless steel is preferable.

Figure 3B:
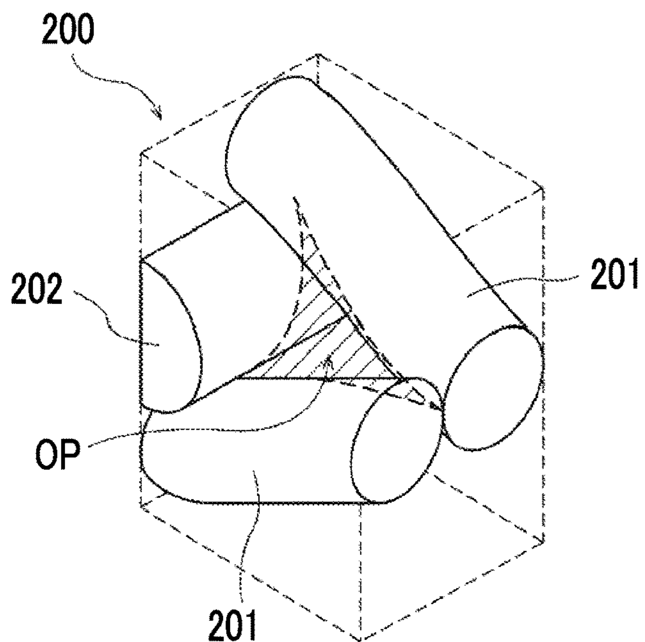
FIG. 3B is an enlarged perspective view showing an opening of the twill woven mesh.

FIG. 3B is an enlarged perspective view showing an opening OP of the twill woven mesh 200. The opening OP of the twill woven mesh 200 is formed by a gap generated by the weaving of two weft yarns 201 and one warp yarn 202. An average hole diameter of the opening OP of the twill woven mesh 200 is calculated as a particle diameter at which a blocking percentage becomes 95% (that is, a separated particle diameter by 95% by a particle permeation test) by performing a filtration test using standard particles.

In addition, in a case where a filter membrane is a microfiltration membrane or an ultrafiltration membrane, an average hole diameter can be measured by a mercury intrusion method. For example, an average hole diameter can be measured by pressing mercury into a filter at high pressure by using Autopore IV 9520 manufactured by Shimadzu Corporation. In a case where it is difficult to measure an average hole diameter by the mercury intrusion method, as described above, an average hole diameter of an ultrafiltration membrane can be calculated based on a molecular weight cut-off.

Figure 3C:
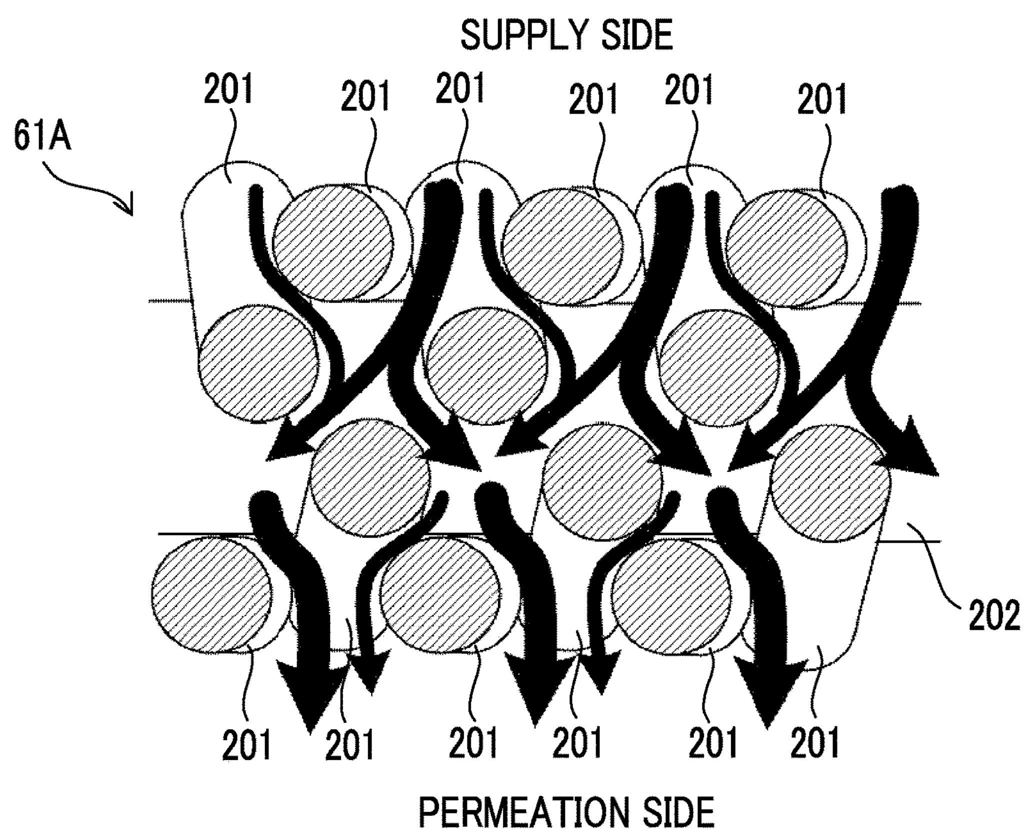
FIG. 3C is a view showing a flow of a fluid permeated through the twill woven mesh.

FIG. 3C is a view showing a cross-sectional structure of the twill woven mesh 200. In FIG. 3C, a flow of a fluid permeated through the twill woven mesh 200 is indicated by arrows. Because the twill woven mesh 200 does not have see-through hole penetrating linearly in a thickness direction, the fluid permeated through the twill woven mesh 200 flows toward the permeation side while changing a flow direction. Accordingly, particles having a relatively large diameter which are contained in the fluid tend to remain on the supply side without flowing out to the permeation side. In other words, by using the twill woven mesh 200 as the first filter membrane 24, the outflow of cells to the permeation side can be suppressed in the membrane separation treatment of the cell suspension, as in the case of the typical structure shown in FIG. 2.

As shown in FIG. 1, the permeation side of the first filter part 20 is connected to a supply side 32 of the second filter part 30 via the flow path 53. In the middle of the flow path 53, valves V1 and V2 and a pump P2 are provided. The valves V1 and V2 are controlled to be in an open state in a case where a permeated liquid permeated through the first filter membrane 24 is sent from the first filter part 20 to the second filter part 30. In other cases, the valves V1 and V2 are in a closed state.

The second filter part 30 includes a vessel 31; and the second filter membrane 34 that separates a space within the vessel 31 into the supply side 32 and a permeation side 33 and performs membrane separation treatment on a permeated liquid permeated through the first filter membrane 24. In addition, the second filter part 30 has, on the supply side 32, an inlet port 30*a* through which a cell suspension flows in. The permeated liquid permeated through the first filter membrane 24 flows into the inside of the vessel 31 from the inlet port 30*a*. In the present embodiment, the second filter part 30 performs membrane separation treatment according to a dead-end system in which substantially the entire amount of a liquid on the supply side 32 is filtered.

Relatively large-sized components contained in the permeated liquid permeated through the first filter membrane 24 are not permeated through the second filter membrane 34 and remain on a membrane surface of the second filter membrane 34 or on the supply side 32 of the second filter part 30. On the other hand, relatively small-sized components contained in the permeated liquid permeated through the first filter membrane 24 are permeated through the second filter membrane 34 to reach the permeation side 33. An exhaust port 30*c* is provided on the permeation side 33 of the second filter part 30, and a flow path 54 is connected to the exhaust port 30*c*. Components permeated through the second filter membrane 34 are discharged from the exhaust port 30*c* to the outside of the vessel 31, and returns to the culture vessel 10 via the flow path 54. The flow path 54 is an example of the second circulation flow path in the disclosed technology. One end there of is connected to the permeation side 33 of the second filter part 30 and the other end is connected to the culture vessel 10.

In the cell culture apparatus 100 according to the present embodiment, the second filter membrane 34 is used for a purpose of separating a medium, and unnecessary components for culture including antibodies, which are contained in the permeated liquid permeated through the first filter membrane 24. In other words, the second filter membrane 34 has a separation performance suitable for blocking permeation of unnecessary components for cell culture including antibodies.

An average hole diameter of the second filter membrane 34 is preferably 1 μm or smaller, is more preferably 0.1 μm or smaller, is even more preferably 0.05 μm or smaller, and is most preferably 0.01 μm or smaller. In a case where an average hole diameter of the second filter membrane 34 is 1 μm or smaller, it is possible to reduce the risk of components, which are unnecessary for cell culture including antibodies, returning to the culture vessel 10 via the flow path 54. In a case of using a mesh, an average hole diameter of the second filter membrane 34 can be measured at a separated particle diameter by 95%. In a case of using a microfiltration membrane or an ultrafiltration membrane, an average hole diameter of the second filter membrane 34 can be measured by a mercury intrusion method.

In addition, in a case where an average hole diameter of the first filter membrane 24 is A, and an average hole diameter of the second filter membrane 34 is B, an average hole diameter ratio (B/A) of both average hole diameters preferably satisfies Equation (1).

$$0<B/A\geq 0.5 \qquad (1)$$

An average hole diameter ratio (B/A) of the first filter membrane 24 and the second filter membrane 34 is more preferably 0.0001 to 0.3, is even more preferably 0.001 to 0.2, and is most preferably 0.001 to 0.1. In a case where an average hole diameter ratio (B/A) of the first filter membrane 24 and the second filter membrane 34 is 0.5 or less, it is possible to reduce the risk of unnecessary components for cell culture returning to the culture vessel 10.

A hollow fiber microfiltration membrane can be used as the second filter membrane 34. By using the hollow fiber microfiltration membrane as the second filter membrane 34, it is possible to reduce the risk of occurrence of clogging as compared with a case of using a hollow fiber ultrafiltration membrane.

In addition, a hollow fiber ultrafiltration membrane is used as the second filter membrane 34 in one embodiment of the present disclosure. By using the hollow fiber ultrafiltration membrane as the second filter membrane 34, unnecessary components for cell culture including antibodies can be effectively captured as compared with the case of using the hollow fiber microfiltration membrane.

In a case of using the hollow fiber ultrafiltration membrane as the second filter membrane 34, a molecular weight cut-off of the hollow fiber ultrafiltration membrane is preferably 100 kDa or less, is more preferably 1 kDa to 90 kDa, is even more preferably 10 kDa to 80 kDa, is particularly preferably 30 kDa to 70 kDa, and is most preferably 60 kDa to 70 kDa. In a case where a molecular weight cut-off of the hollow fiber ultrafiltration membrane used as the second filter membrane 34 is 100 kDa or less, unnecessary components for cell culture including antibodies can be captured more effectively. In addition, although growth factors such as cytokines are released from cells, allowing the growth factors to return to a culture tank as much as possible has a better effect on cell growth properties. Because a molecular weight of a growth factor is about 1000 to 30000, it is preferable to set a lower limit of a molecular weight cut-off of the second filter membrane 34 to a molecular weight cut-off equal to or higher than a molecular weight of a growth factor.

A molecular weight cut-off of the hollow fiber ultrafiltration membrane is calculated from a molecular weight corresponding a molecular weight at which a blocking percentage becomes 90% by permeating of a standard substance having a known molecular weight.

In the middle of the flow path 54, a valve V3 is provided in the vicinity of the permeation side 33 of the second filter part 30. The valve V3 is controlled to be in an open state in a case where components permeated through the second filter membrane 34 are sent to the culture vessel 10. In other cases, the valve V3 is in a closed state.

The cell culture apparatus 100 according to the present embodiment has a recovery means for recovering unnecessary components for cell culture including antibodies, which are blocked by the second filter membrane 34. The above-described recovery means is configured to include a backwash flow path 55, a pump P3, recovery flow paths 56 and 57, and a recovery tank 40. The pump P3 is an example of a liquid sending part in the disclosed technology.

The backwash flow path 55 forms a bypass flow path that bypasses an inlet side and an outlet side of the valve V3. The pump P3 is provided in the middle of the backwash flow path 55, and performs backwash treatment of the second filter membrane 34 by generating a liquid flow from the permeation side 33 to the supply side 32 of the second filter part 30, which is an opposite flow of a liquid flow generated during general membrane separation treatment. While the backwash treatment is performed, the valve V3 is controlled to be in a closed state, and a liquid used for backwash flows through the backwash flow path 55 to be supplied to the second filter membrane 34. In a case of performing the backwash treatment on the second filter membrane 34, unnecessary components for culture including antibodies which remain on the membrane surface of the second filter membrane 34 and the supply side 32 of the second filter part 30, are discharged from the inlet port 30*a* of the second filter part 30.

In the vicinity of the inlet port 30*a* of the second filter part 30, the recovery flow path 56 is connected to the flow path 53 that connects the permeation side 23 of the first filter part 20 and the supply side 32 of the second filter part 30. While the backwash treatment is performed, the valves V1, V2, and V3 are controlled to be in a closed state, and a valve V4 is controlled to be in an open state. Accordingly, unnecessary components for culture including antibodies, which are discharged from the inlet port 30*a* of the second filter part 30 by the backwash treatment, are stored in the recovery tank 40 via the recovery flow path 56. Unnecessary components for culture including antibodies, which are contained in the recovery tank 40, are sent to an antibody purification step, which is the next step, via the recovery flow path 57.

The cell culture apparatus 100 has a medium supply flow path 58 for supplying a fresh medium to the culture vessel 10, and a pump P4 provided in the middle of the medium supply flow path 58. In addition, in the cell culture apparatus 100, in order to prevent a concentration of cells in the culture vessel 10 from becoming excessively high, cell breeding treatment in which some of cells in the culture vessel 10 (for example, about 10%) are extracted is performed at an appropriate timing within a culture period. In the cell breeding treatment, cells in the culture vessel 10 are discharged to the outside of the culture vessel 10 via a flow path 59. Furthermore, the cell culture apparatus 100 has a controller (not shown) that controls the pumps P1 to P4 and the valves V1 to V4.

Hereinafter, the operation of the cell culture apparatus 100 will be described.

In the cell culture apparatus 100, in a case where the membrane separation treatment is performed in the first filter part 20 and the second filter part 30, the pumps P1 and P2 are in a driven state, and the pump P3 is in a stopped state. In addition, the valves V1, V2, and V3 are controlled to be in an open state, and the valve V4 is controlled to be in a closed state.

By driving the pump P1, the cell suspension stored in the culture vessel 10 is sent to the supply side 22 of the first filter part 20. The cell suspension extracted from the culture vessel 10 is subjected to the membrane separation treatment according to a tangential flow system by using the first filter membrane 24. Cells blocked by the first filter membrane 24 return to the culture vessel 10 via the flow path 52. On the other hand, unnecessary components for culture including antibodies are permeated through the first filter membrane 24.

The permeated liquid permeated through the first filter membrane 24 is sent to the supply side 32 of the second filter part 30 via the flow path 53. The permeated liquid permeated through the first filter membrane 24 is subjected to membrane separation treatment according to a dead-end system by using the second filter membrane 34. Unnecessary components for cell culture including antibodies, which are blocked by the second filter membrane 34, remain on the membrane surface of the second filter membrane 34 or on the supply side 32 of the second filter part 30. Meanwhile, a clean medium, which is obtained by permeating of unnecessary components for cell culture such as antibodies through the second filter membrane 34 and removing them, returns to the culture vessel 10 via the flow path 54.

On the other hand, in a case of performing the backwash treatment in the cell culture apparatus 100, the pump P3 is in a driven state, and the pumps P1 and P2 are in a stopped state. In addition, the valve V4 is controlled to be in an open state, and the valves V1, V2, and V3 are controlled to be in a closed state.

By driving the pump P3, a liquid flow from the permeation side to the supply side of the second filter part 30, which is an opposite flow of a liquid flow generated during general membrane separation treatment, is generated. Therefore, backwash treatment of the second filter membrane 34 is performed. In a case of performing the backwash treatment on the second filter membrane 34, unnecessary components for cell culture including antibodies, which remain on the membrane surface of the second filter membrane 34 and the supply side 32 of the second filter part 30, are discharged from the inlet port 30*a* of the second filter part 30. Unnecessary components for cell culture including antibodies, which are discharged from the second filter part 30 by the backwash treatment, are stored in the recovery tank 40 via the recovery flow path 56. Unnecessary components for culture including antibodies, which are contained in the recovery tank 40, are sent to an antibody purification step, which is the next step, via the recovery flow path 57. During the culture period, the pump P3 is intermittently in a driven state, and thus the backwash treatment is intermittently performed. Accordingly, liquid sending of unnecessary components for the cell culture including the antibody to the recovery flow path 56 is performed intermittently. In the cell culture apparatus 100 according to the present embodiment, the membrane separation treatment and the backwash treatment are alternately and repeatedly performed during the culture period.

The pump P2 is driven continuously or at a predetermined timing while the membrane separation treatment and the backwash treatment are being performed, and a fresh medium of an approximately the same amount as an amount of a medium sent to the recovery tank 40 via the recovery flow path 56 is supplied to the culture vessel 10 via the medium supply flow path 58. Accordingly, an amount of a medium in the culture vessel 10 is maintained substantially constant during the culture period.

The cell culture apparatus 100 according to the present embodiment operates as described above to realize cell culture by a cell culture method including the following steps. A first membrane separation step of using the first filter membrane 24 to perform membrane separation treatment on a cell suspension extracted from the culture vessel 10 that stores the cell suspension containing cells, and allowing components blocked by the first filter membrane 24 to return to the culture vessel 10. A second membrane separation step of using the second filter membrane 34 to perform membrane separation treatment on components permeated through the first filter membrane 24, and allowing components permeated through the second filter membrane 34 to return to the culture vessel 10. A recovery step of recovering components blocked by the second filter membrane 34 via the recovery flow path 56.

In a case where a perfusion ratio is X and a circulation ratio is Y in the cell culture apparatus 100, a ratio Y/X of the perfusion ratio X to the circulation ratio Y is preferably within a range represented by Equation (2).

$$1.5 \leq Y/X \quad (2)$$

A perfusion ratio X is a ratio p/q (X=p/q) of an amount p of components (medium) recovered via the recovery flow path 56 per day to an amount q of the cell suspension stored in the culture vessel 10. An amount p of components recovered via the recovery flow path 56 per day corresponds to an amount of medium supplied via the medium supply flow path 58 per day.

A circulation ratio Y is a ratio r/q (Y=r/q) of an amount r of components (medium) permeated through the first filter membrane 24 per day to an amount q of the cell suspension stored in the culture vessel 10. In other words, the ratio Y/X of the perfusion ratio X to the circulation ratio Y corresponds to a ratio r/p (Y/X=r/p) of an amount r of components permeated through the first filter membrane 24 per day to an amount p of components recovered via the recovery flow path 56 per day.

As shown in Equation (2), the ratio Y/X of the perfusion ratio X to the circulation ratio Y is preferably 1.5 or more, is more preferably 2 to 20, is even more preferably 2.5 to 15, and is most preferably 3 to 10. In a case where the ratio Y/X of the perfusion ratio X to the circulation ratio Y is 1.5 or more, it is possible to sufficiently remove unnecessary components for cell culture including antibodies.

In addition, the perfusion ratio X is preferably 0.1 to 2, is more preferably 0.2 to 1.5, and is even more preferably 0.3 to 1. In a case where the perfusion ratio is 0.1 or more, the risk of occurrence of clogging of the second filter membrane 34 can be reduced. Furthermore, in a case where the perfusion ratio is 2 or less, an amount of medium used can be reduced, and culture at low cost can be achieved.

Furthermore, the circulation ratio Y is preferably 0.2 to 10, is more preferably 0.5 to 8, and is even more preferably 1 to 6. In a case where the circulation ratio is 0.2 or more, it is possible to sufficiently remove unnecessary components for culture including antibodies. Furthermore, in a case where the circulation ratio is 10 or less, the risk of occurrence of clogging in the first filter membrane 24 and the second filter membrane 34 can be reduced.

Furthermore, a concentration of cells contained in the cell suspension stored in the culture vessel 10 is preferably $2\times10^7$ cells/ml or more, is more preferably $5\times10^7$ cells/ml to $20\times10^7$ cells/ml, and is even more preferably $8\times10^7$ cells/ml to $15\times10^7$ cells/ml. In a case where a concentration of cells contained in the cell suspension stored in the culture vessel 10 is $2\times10^7$ cells/ml or more, a sufficient amount of antibodies can be recovered.

Furthermore, a concentration of fine particles, which have a particle diameter of 2 μm to 4 μm and are contained in the cell suspension stored in the culture vessel 10, is preferably $40\times10^7$ particles/ml or less, is more preferably $20\times10^7$ particles/ml or less, is even more preferably $10\times10^7$ particles/ml or less, and is most preferably $0.1\times10^7$ particles/ml to $5\times10^7$ particles/ml. In a case where a concentration of fine particles, which have a particle diameter of 2 μm to 4 μm and are contained in the cell suspension stored in the culture vessel 10, is $40\times10^7$ particles/ml or less, cell growth properties can be improved.

Furthermore, in the membrane separation treatment by the first filter membrane 24, a permeation rate of cells is preferably 20% or less, is more preferably 10% or less, is even more preferably 5% or less, and is most preferably 2% or less. In the membrane separation treatment by the first filter membrane 24, in a case where a permeation rate of cells is 20% or less, a decrease in the number of cells in the culture vessel 10 can be suppressed.

Furthermore, in the membrane separation treatment by the first filter membrane 24, a permeation rate of fine particles having a particle diameter of 2 μm to 4 μm is preferably 30% or more, is more preferably 50% or more, and is even more preferably 70% or more. In the membrane separation treatment by the first filter membrane 24, in a case where a permeation rate of fine particles having a particle diameter of 2 μm to 4 μm is 30% or more, it is possible to promote removal of unnecessary components for cell culture in the culture vessel 10.

Furthermore, a concentration of fine particles, which have a particle diameter of 2 μm to 4 μm and are contained in components permeated through the second filter membrane 34, is preferably $1\times10^7$ particles/ml or less, is more preferably $0.1\times10^7$ particles/ml or less, and is even more preferably $0.01\times10^7$ particles/ml or less. In a case where a concentration of fine particles, which have a particle diameter of 2 μm to 4 μm and are contained in components permeated through the second filter membrane 34, is $1\times10^7$ particles/ml or less, it is possible to reduce an amount of unnecessary components for cell culture returning to the culture vessel 10.

Furthermore, a concentration of antibodies contained in the cell suspension stored in the culture vessel 10 is preferably 4 g/l or less, is more preferably 3 g/l or less, is even more preferably 2 g/l or less, and is particularly preferably 1 g/l or less. In a case where a concentration of antibodies contained in the cell suspension stored in the culture vessel 10 is 4 g/l or less, it is possible to suppress cell aggregation and to improve cell growth properties.

Furthermore, in the membrane separation treatment by the first filter membrane 24, a permeation rate of antibodies is preferably 30% or more, is more preferably 50% or more, and is even more preferably 70% or more. In the membrane separation treatment by the first filter membrane 24, in a case where a permeation rate of antibodies is 30% or more, it is possible to reduce a concentration of antibodies in the cell suspension stored in the culture vessel 10, and to improve cell growth properties.

Furthermore, a concentration of antibodies contained in components permeated through the second filter membrane 34 is preferably 1 g/l or less, is more preferably 0.5 g/l or less, and is even more preferably 0.1 g/l or less. In a case where a concentration of antibodies contained in components permeated through the second filter membrane 34 is 1 g/l or less, it is possible to reduce an amount of antibodies returning to the culture vessel 10.

Furthermore, a concentration of antibodies contained in components blocked by the second filter membrane is preferably 0.5 g/l or more, is more preferably 1 g/l, and is even more preferably 2 g/l. In a case where a concentration of antibodies contained in components blocked by the second filter membrane is 0.5 g/l or more, it is possible to recover a sufficient amount of antibodies.

As described above, according to the cell culture apparatus 100 according to the present embodiment, the first filter membrane 24 is used to perform membrane separation treatment on a cell suspension extracted from the culture vessel 10, and components blocked by the first filter membrane 24 returns to the culture vessel 10. Accordingly, it is possible to remove unnecessary components for cell culture, such as dead cells, crushed cells, DNA, HCP, antibodies, and waste products from the cell suspension stored in the culture vessel 10. In a case where cells are cultured in a medium containing dead cells or crushed cells, the cells become anaerobic, and thus cell growth properties deteriorate. Meanwhile, in a case where cells are cultured in a medium containing DNA, HCP, antibodies, and waste products, the cells adhere to each other, cell aggregates are generated, and thus cell growth properties deteriorate. Furthermore, in a case where DNA, HCP, antibodies, and waste products accumulate in the culture vessel 10, the inside of the culture vessel 10 is contaminated, thereby making culture for a long period of time difficult. According to the cell culture apparatus 100 of the present embodiment, it is possible to remove unnecessary components for cell culture such as dead cells, crushed cells, DNA, HCP, antibodies, and waste products from the cell suspension stored in the culture vessel 10 by the membrane separation treatment using the first filter membrane 24. Therefore, it is possible to improve growth properties of cells cultured in the culture vessel 10. In addition, by improving cell growth properties, it is possible to improve antibody productivity.

Furthermore, by adopting the tangential flow system as a system of the membrane separation treatment by the first filter membrane 24, it is possible to reduce damage to cells as compared to a case of adopting the dead-end system. It is also possible to adopt the dead-end system as a system of the membrane separation treatment by the first filter membrane 24.

Furthermore, according to the cell culture apparatus 100 according to the present embodiment, a membrane separation treatment is performed by using the second filter membrane 34 on a permeated liquid permeated through the first filter membrane 24, and the permeated liquid permeated through the second filter membrane 34 returns to the culture vessel 10. Accordingly, unnecessary components for cell culture such as dead cells, crushed cells, DNA, HCP, antibodies, and waste products are removed from the permeated liquid permeated through the first filter membrane 24, and a clean medium from which the unnecessary components have been removed returns to the culture vessel 10. As described above, the clean medium discharged to the permeation side 33 of the second filter membrane 34 returns to the culture vessel 10, and therefore an amount of medium used can be reduced. Meanwhile, antibodies secreted from cells can be captured by the second filter membrane 34.

Furthermore, according to the cell culture apparatus 100 according to the present embodiment, components blocked by the second filter membrane 34 are recovered via the recovery flow path 56. Accordingly, it is possible to recover antibodies blocked by the second filter membrane 34.

As described above, according to the cell culture apparatus 100 according to the present embodiment, it is possible to improve antibody productivity while reducing an amount of medium used. In one embodiment, the above-described effects are promoted by selecting an average hole diameter of each filter membrane such that an average hole diameter of the first filter membrane 24 is 20 μm or smaller, and $0<B/A\leq0.5$ is satisfied in a case where an average hole diameter of the first filter membrane 24 is A and an average hole diameter of the second filter membrane 34 is B. In another embodiment, the above-described effects are promoted by setting an average hole diameter of the first filter membrane 24 to 20 μm or less and using the second filter membrane 34 as an ultrafiltration membrane.

As described above, since the cell culture apparatus 100 according to the present embodiment has the recovery flow path 56 for recovering components blocked by the second filter membrane 34, it is possible to recover antibodies blocked by the second filter membrane 34. Furthermore, by considering an average hole diameter A of the first filter membrane 24, a ratio (B/A) of an average hole diameter B of the second filter membrane 34 to an average hole diameter A, or the type of the second filter membrane 34, it is possible to reduce a possibility of escaping of necessary cells for culture to the outside of a system; insufficient discharge of unnecessary components for cell culture such as dead cells, crushed cells, DNA, HCP, antibodies, and waste products to the outside of the system; and not being able to efficiently recover antibodies. For example, in a case where an average hole diameter A of the first filter membrane 24 is 20 μm or less, it is possible to suppress cells from being permeated through the first filter membrane 24 and the cells from escaping to the outside of the system via the recovery flow path 57. Furthermore, by selecting an average hole diameter of each filter membrane to satisfy $0<B/A\leq0.5$, or by using the second filter membrane 34 as an ultrafiltration membrane, it is possible to reduce a possibility of not being able to sufficiently block, by the second filter membrane 34, unnecessary components for the culture which are permeated through the first filter membrane 24. In other words, not only proving the recovery flow path 56 that recovers components blocked by the second filter membrane 34, but also using the second filter membrane 34 as an ultrafiltration membrane under the conditions in which an average hole diameter of the first filter membrane 24 is 20 μm or smaller, and a ratio B/A of an average hole diameter A of the first filter membrane 24 to an average hole diameter B of the second filter membrane 34 is $0<B/A\leq0.5$; or under the condition in which an average hole diameter of the first filter membrane 24 is 20 μm or smaller, is important.

In general, it is very difficult to continuously recover components blocked by a filter membrane while continuously filtering a liquid containing various components, such as a culture solution, by using the filter membrane. Even in a case where components blocked by the second filter membrane 34 are recovered by backwash as in the cell culture apparatus 100 according to the present embodiment, it is assumed that a gel layer is formed on the second filter membrane 34, and furthermore, clogging occurs, and therefore filtration becomes enabled to be performed within few days. In second and third embodiments to be described later, membrane separation treatment by the second filter membrane 34 is performed according to the tangential flow system, but even in this case, the same problems may occur. As in the cell culture apparatus 100 according to the present embodiment, by using the second filter membrane 34 as an ultrafiltration membrane under the conditions in which an average hole diameter of the first filter membrane 24 is 20 μm or smaller, and a ratio B/A of an average hole diameter A of the first filter membrane 24 to an average hole diameter B of the second filter membrane 34 is $0<B/A\leq0.5$; or under the condition in which an average hole diameter of the first filter membrane 24 is 20 μm or smaller, it is possible to perform filtration and culture for a long period of time while suppressing formation of gel layers and clogging.

Furthermore, according to the cell culture apparatus 100 according to the present embodiment, it is possible to increase a concentration of antibodies that are contained in the recovery tank 40 and sent to the purification step. Therefore, it is possible to reduce treatment cost in the antibody purification step. Furthermore, in the cell breeding treatment, a concentration of antibodies can be lowered in a medium to be extracted from the culture vessel 10 or a medium remaining in the culture vessel 10 after the completion of the cell culture. Therefore, it is possible to reduce disposal loss of antibodies which is associated with disposal of these media.

Furthermore, according to the cell culture apparatus 100 according to the present embodiment, residence time of antibodies in the culture vessel 10 can be shortened. Therefore, it is possible to suppress a deterioration in antibody quality due to aggregation or degradation of antibodies in the culture vessel. In a case where a ratio Y/X which is a ratio of a circulation ratio to a perfusion ratio is, for example, 10, residence time of antibodies in a culture tank can be reduced to about 1/10 compared to a case where the second filter membrane is not installed.

In addition to the disclosed technique, as a measure to shorten residence time of antibodies in a culture tank, it is also possible to periodically perform elution and recovery of antibodies by performing centrifugation instead of providing the first filter membrane, by performing centrifugation instead of the second filter membrane, or by performing affinity chromatography that adsorbs antibodies. However, in any of these measures, continuous treatment is difficult, which makes the disclosed technology excellent.

Second Embodiment

Figure 4:
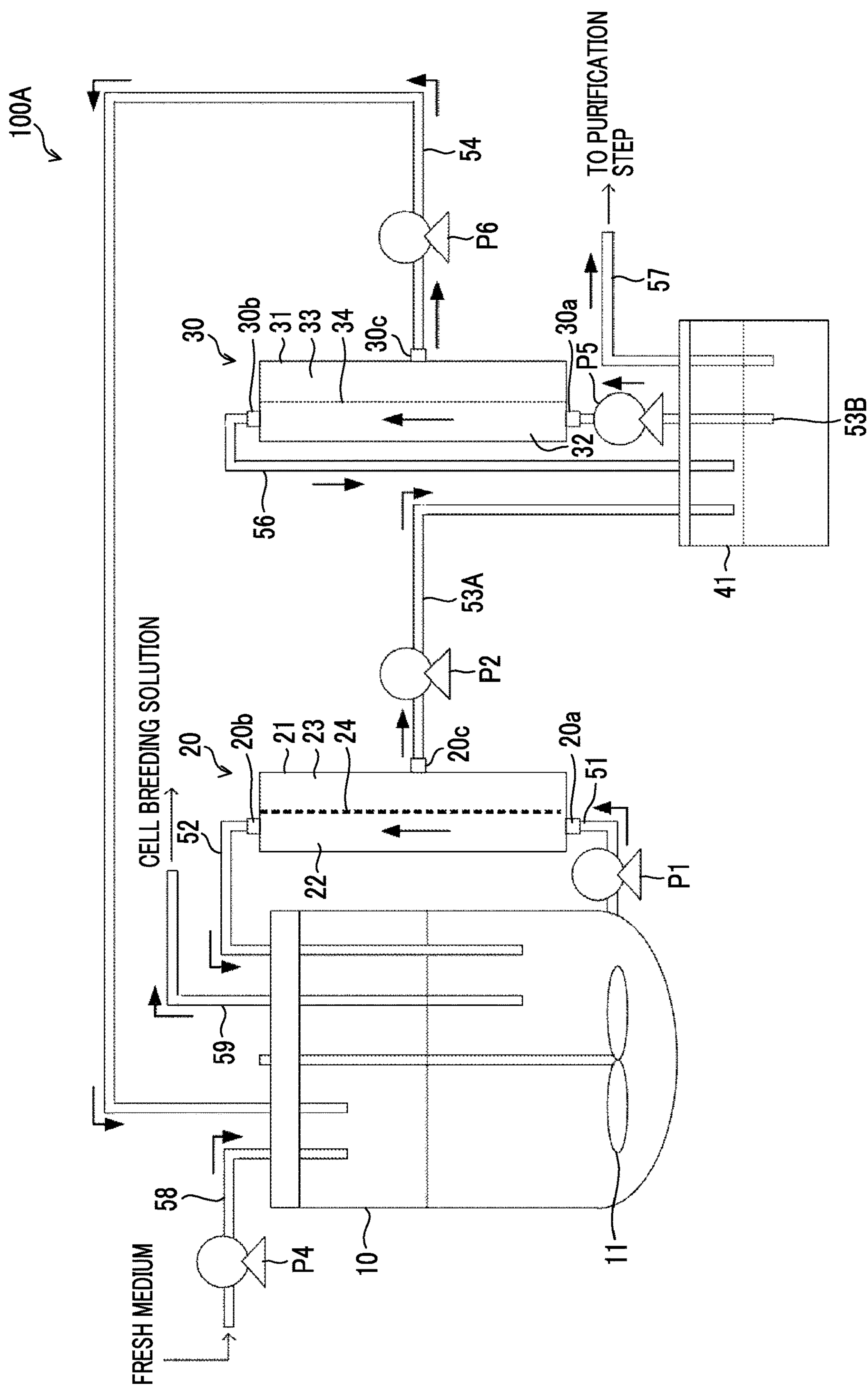
FIG. 4 is a view showing a configuration of a cell culture apparatus according to a second embodiment of the disclosed technology.

FIG. 4 is a view showing a configuration of a cell culture apparatus 100A according to a second embodiment of the disclosed technology. The cell culture apparatus 100A is different from the cell culture apparatus 100 according to the first embodiment in that a system of membrane separation treatment in the second filter part 30 is a tangential flow system, and in an aspect of recovery of components blocked by the second filter membrane 34.

In the cell culture apparatus 100 according to the present embodiment, the other end of a flow path 53A whose one end is connected to the permeation side 23 of the first filter membrane 24 is connected to a tank 41.

One end of a flow path 53B is connected to the tank 41, and the other end is connected to the inlet port 30*a* of the second filter part 30. In the middle of the flow path 53B, a pump P5 that extracts a liquid contained in the tank 41 and sends the liquid to the second filter part 30 is provided.

The second filter part 30 has the inlet port 30*a* and an outlet port 30*b* on the supply side 32. The liquid extracted from the tank 41 passes through the second filter membrane 34 while flowing from the inlet port 30*a* into the inside of the vessel 31 and flowing from the outlet port 30*b* to the outside of the vessel 31. The second filter part 30 performs membrane separation treatment by using the second filter membrane 34 according to a tangential flow system, on a liquid that is a target of the membrane separation treatment.

One end of the recovery flow path 56 is connected to the outlet port 30*b* of the second filter part 30, and the other end is connected to the tank 41. Components blocked by the second filter membrane 34 in a liquid extracted from the tank 41 are sent to the antibody purification step which is the next step via the recovery flow path 57. The second filter part 30 has the exhaust port 30*c* on the permeation side 33. The flow path 54 is connected to the exhaust port 30*c*.

Hereinafter, the operation of the cell culture apparatus 100A will be described.

In the cell culture apparatus 100A, in a case where the membrane separation treatment is performed in the first filter part 20 and the second filter part 30, pumps P1, P2, P4, P5, and P6 are in a driven state.

By driving the pump P1, the cell suspension stored in the culture vessel 10 is sent to the supply side 22 of the first filter part 20. The cell suspension extracted from the culture vessel 10 is subjected to membrane separation treatment by flowing along the membrane surface of the first filter membrane 24. Cells blocked by the first filter membrane 24 return to the culture vessel 10 via the flow path 52. On the other hand, unnecessary components for cell culture including antibodies are permeated through the first filter membrane 24.

A permeated liquid permeated through the first filter membrane 24 is sent to the tank 41 via the flow path 53A. The permeated liquid which is contained in the tank 41 and permeated through the first filter membrane 24 is extracted by the pump P5, and sent to the supply side 32 of the second filter part 30. The permeated liquid permeated through the first filter part 20 is subjected to membrane separation treatment by flowing along the membrane surface of the second filter membrane 34. Unnecessary components for cell culture including antibodies, which are blocked by the second filter membrane 34, are sent to the tank 41 via the recovery flow path 56. By continuously performing the membrane separation treatment in the second filter part 30, a concentration of antibodies in the tank 41 is raised to a desired concentration. A medium containing concentrated antibodies is sent to the antibody purification step, which is the next step, via the recovery flow path 57. In the cell culture apparatus 100 according to the first embodiment described above, components blocked by the second filter membrane 34 are intermittently sent to the recovery flow path 56, whereas in the cell culture apparatus 100A according to the present embodiment, components blocked by the second filter membrane 34 are continuously sent to the recovery flow path 56. Meanwhile, a clean medium, which is obtained by permeating of unnecessary components for cell culture such as antibodies through the second filter membrane 34 and removing them, is discharged from the exhaust port 30*c* to the outside of the second filter part 30, and returns to the culture vessel 10 via the flow path 54.

By driving the pump P4, the medium is supplied to the culture vessel 10 via the medium supply flow path 58, and therefore an amount of the medium in the culture vessel 10 is maintained substantially constant during the culture period.

According to the cell culture apparatus 100A according to the present embodiment, since a system of the membrane separation treatment in the second filter part 30 is a tangential flow system, backwash treatment is not required in a case of recovering components blocked by the second filter part 30.

In the cell culture apparatus 100A according to the present embodiment, since a system of the membrane separation treatment in the second filter part 30 is a tangential flow system, it is possible to reduce pressure applied to antibodies, and to suppress a deterioration in quality antibodies, as compared to a case where membrane separation treatment is performed according to a dead-end system. In addition, by using the tangential flow system as a system of the membrane separation treatment in the second filter part 30, it is possible to reduce the risk of occurrence of clogging in the second filter membrane 34, as compared to a case of performing membrane separation treatment according to the dead-end system.

Furthermore, according to the cell culture apparatus 100A according to the present embodiment, it is possible to increase a concentration of antibodies in the tank 41 to a desired concentration by continuously performing the membrane separation treatment in the second filter part 30, and it is possible to send a medium containing concentrated antibodies to the purification step via the recovery flow path 57. Accordingly, load on treatment in the purification step can be reduced.

Third Embodiment

Figure 5:
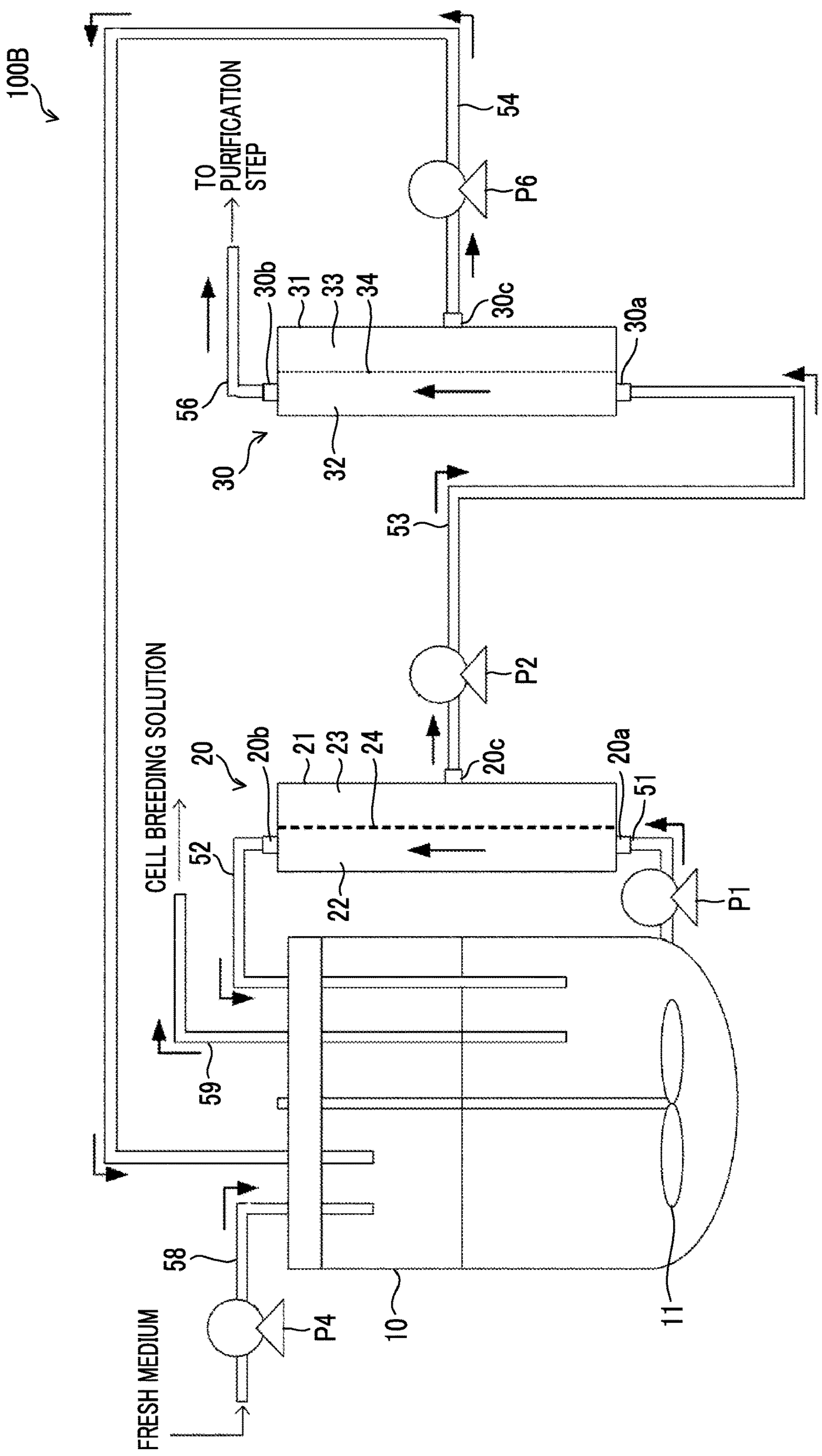
FIG. 5 is a view showing a configuration of a cell culture apparatus according to a third embodiment of the disclosed technology.

FIG. 5 is a view showing a configuration of a cell culture apparatus 100B according to a third embodiment of the disclosed technology. The cell culture apparatus 100B is different from the cell culture apparatus 100 according to the first embodiment in that a system of membrane separation treatment in the second filter part 30 is a tangential flow system, and in an aspect of recovery of components blocked by the second filter membrane 34.

In the cell culture apparatus 100B according to the present embodiment, the other end of the flow path 53 whose one end is connected to the permeation side 23 of the first filter membrane 24 is connected to the inlet port 30*a* of the second filter part 30.

The second filter part 30 has the inlet port 30*a* and the outlet port 30*b* on the supply side 32. A permeated liquid permeated through the first filter membrane 24 passes through the second filter membrane 34 while flowing from the inlet port 30*a* into the inside of the vessel 31 and flowing from the outlet port 30*b* to the outside of the vessel 31. The second filter part 30 performs membrane separation treatment by using the second filter membrane 34 according to a tangential flow system, on a liquid that is a target of the membrane separation treatment. The recovery flow path 56 is connected to the outlet port 30*b* of the second filter part 30. The second filter part 30 has the exhaust port 30*c* on the permeation side 33. The flow path 54 is connected to the exhaust port 30*c*.

Hereinafter, the operation of the cell culture apparatus 100B will be described.

In the cell culture apparatus 100B, in a case where the membrane separation treatment is performed in the first filter part 20 and the second filter part 30, pumps P1, P2, P4, and P6 are in a driven state.

By driving the pump P1, the cell suspension stored in the culture vessel 10 is sent to the supply side 22 of the first filter part 20. The cell suspension extracted from the culture vessel 10 is subjected to membrane separation treatment by flowing along the membrane surface of the first filter membrane 24. Cells blocked by the first filter membrane 24 return to the culture vessel 10 via the flow path 52. On the other hand, unnecessary components for culture including antibodies are permeated through the first filter membrane 24.

The permeated liquid permeated through the first filter membrane 24 is extracted by the pump P2, and sent to the supply side 32 of the second filter part 30. The permeated liquid permeated through the first filter part 20 is subjected to membrane separation treatment by flowing along the membrane surface of the second filter membrane 34. Unnecessary components for cell culture including antibodies, which are blocked by the second filter membrane 34, are sent to the antibody purification step which is the next step via the recovery flow path 56. In the cell culture apparatus 100 according to the first embodiment described above, components blocked by the second filter membrane 34 are intermittently sent to the recovery flow path 56, whereas in the cell culture apparatus 100B according to the present embodiment, components blocked by the second filter membrane 34 are continuously sent to the recovery flow path 56. Meanwhile, a clean medium, which is obtained by permeating of unnecessary components for cell culture such as antibodies through the second filter membrane 34 and removing them, is discharged from the exhaust port 30*c* to the outside of the second filter part 30, and returns to the culture vessel 10 via the flow path 54.

By driving the pump P4, a fresh medium of an approximately the same amount as an amount of a medium that contains antibodies sent to the purification step via the recovery flow path 56 is supplied to the culture vessel 10 via the medium supply flow path 58. Accordingly, an amount of a medium in the culture vessel 10 is maintained substantially constant during the culture period.

According to the cell culture apparatus 100B according to the present embodiment, since a system of the membrane separation treatment in the second filter part 30 is a tangential flow system, backwash treatment is not required in a case of recovering components blocked by the second filter part 30.

In addition, according to the cell culture apparatus 100B according to the present embodiment, it is possible to reduce pressure applied to antibodies, and to suppress a deterioration in quality antibodies, as compared to a case where membrane separation treatment is performed according to a dead-end system. Furthermore, it is possible to reduce the risk of occurrence of clogging in the second filter membrane 34, as compared to a case of performing membrane separation treatment according to the dead-end system.

Furthermore, according to the cell culture apparatus 100B according to the present embodiment, a treatment fluid passed through the second filter part 30 only once is sent to the next step, and therefore it is possible to reduce load on treatment in the second filter part 30, as compared to a case in which a treatment fluid that has passed through the second filter part 30 a plurality of times is sent to the next step. Accordingly, the risk of occurrence of clogging of the second filter membrane 34 can be reduced.

EXAMPLES AND COMPARATIVE EXAMPLES

Cells were cultured by using the cell culture apparatus according to the embodiment of the disclosed technology described above. The results of evaluation of a plurality of items to be described below are shown in FIG. 6A and FIG. 6B. In each example and each comparative example, type of cultured cell, specifications of the first filter membrane 24 and the second filter membrane 34, a membrane separation system, a perfusion ratio, a circulation ratio, a concentration of cells in the culture vessel 10, a concentration of fine particles in the culture vessel 10, and a concentration of antibodies in the culture vessel 10, are as shown in FIG. 6A. Examples 1 to 20 and Comparative Examples 1 and 2 are shown in the embodiment of FIG. 1. Example 21 was implemented by the embodiment shown in FIG. 5. Comparative Examples 3 and 4 were implemented by the embodiment in which the second filter part was removed from the embodiment of FIG. 1. Evaluation items were cell growth properties, an amount of medium used, an aggregate in a culture vessel, a concentration of fine particles in a culture vessel, a concentration of antibodies in a culture vessel, filtration clogging of a first stage, filtration clogging of a second stage, an antibody recovery percentage, a main peak percentage (antibody quality), and comprehensive judgement in which these items were comprehensively judged.

In a case of using a mesh, an average hole diameter of the first filter membrane 24 and the second filter membrane 34 is measured at a separated particle diameter by 95%. In a case of using a microfiltration membrane (MF membrane) or an ultrafiltration membrane (UF membrane), an average hole diameter of the first filter membrane 24 and the second filter membrane 34 was measured by a mercury intrusion method.

In order to control a concentration of cells in the culture vessel 10, cell breeding treatment was performed. A cell breeding ratio is defined as a ratio of an amount of cell breeding solution extracted per day to an amount of cell suspension stored in the culture vessel 10 (an amount of cell breeding solution extracted per day/an amount of cell suspension stored in the culture vessel 10). In Examples 1 to 21 and Comparative Examples 1 to 4, culture was performed at a cell breeding ratio of 0.1.

A diameter of cell and a concentration of cells were measured by using Vi-CELL of BECKMAN COULTER. A concentration of fine particles was measured by using Multisizer 4 of BECKMAN COULTER.

In the measurement of a diameter of cell, cells contained in the cell suspension sampled from the culture vessel 10 were used as measurement targets. In the measurement of a concentration of cells and a concentration of antibodies in the culture vessel 10, the cell suspension sampled from the culture vessel was used as a measurement target.

A permeation rate of cells in the first filter membrane 24 is obtained by converting, to a percentage (%), a ratio d2/d1 of a concentration d1 of cells in a medium before cells are permeated through the first filter membrane 24 to a concentration d2 of cells in the medium after cells are permeated through the first filter membrane 24.

A permeation rate of fine particles in the first filter membrane 24 is obtained by converting, to a percentage (%), a ratio d4/d3 of a concentration d3 of fine particles in a medium before fine particles are permeated through the first filter membrane 24 to a concentration d4 of fine particles in the medium after fine particles are permeated through the first filter membrane 24.

A permeation rate of antibodies in the first filter membrane 24 is obtained by converting, to a percentage (%), a ratio d6/d5 of a concentration d5 of antibodies in a medium before antibodies are permeated through the first filter membrane 24 to a concentration d6 of antibodies in the medium after antibodies are permeated through the first filter membrane 24.

The medium before being permeated through the first filter membrane 24 was sampled from the culture vessel. The medium after cells, fine particles, or antibodies are permeated through the first filter membrane 24 was sampled from the flow path 53 connected to the permeation side of the first filter part 20.

In the measurement of a concentration of fine particles in the permeated liquid that had permeated through the second filter membrane 34, a medium sampled from the flow path 54 connected to the permeation side of the second filter part 30 was used as a measurement target.

In the measurement of a concentration of antibodies contained in a recovery solution, a recovery solution sampled from the recovery flow path 56 was used as a measurement target.

As residence time of antibodies in the culture vessel 10 becomes shorter, antibody quality tends to be improved. As antibody quality, a degradation state and an aggregation state of antibodies were evaluated by size exclusion chromatography according to the following procedure.

(1) 100 μl of Ab Capcher Extra (Protenova Co., Ltd) was added to 7 ml of a permeated liquid or a supernatant liquid obtained by separation treatment, and the mixture was allowed to stand for 30 minutes.

(2) The obtained liquid was centrifuged, the supernatant liquid was discarded, and the precipitated gel was recovered.

(3) The obtained gel was put in Micro Bio-Spin 6 column (Bio-Rad Laboratories, Inc.) set in a 2 ml microtube, 400 μl of elution buffer (0.1 M Glycine-HCl (pH 2.8)) was added thereto, and the mixture was centrifuged.

(4) For neutralization, 30 μl of neutralization buffer (1.0 M Tris-HCl, pH 9.0) was added into the liquid passed through the column and accumulated in the tube.

(5) Using AMICON ULTRA 30 kDa (Merck Corporation), in the obtained neutralized solution, buffer was exchanged with a mixed solution of 80% phosphate buffered saline and 20% ultrapure water, and a solution was prepared such that a concentration of antibodies became 5 mg/L.

(6) Size distribution of antibodies in the prepared solution was measured by size exclusion chromatography (SEC) by using TSKgel G3000SW Column manufactured by TOSOH CORPORATION, and a ratio of a main peak was calculated. As a main peak percentage becomes large, quality of antibodies contained in the permeated liquid or the supernatant liquid is shown to become high.

An antibody recovery percentage is defined by the following equation.

Amount of antibodies recovered from permeated liquid per day/(amount of antibodies recovered from permeated liquid per day+amount of antibodies discarded due to cell breeding per day)×100

Judgment criteria for cell growth properties are as follows.

A: A concentration of cells in a culture vessel is $8\times10^7$ cells/ml or more.

B: A concentration of cells in a culture vessel is $5\times10^7$ cells/ml or more and less than $8\times10^7$ cells/ml.

C: A concentration of cells in a culture vessel is $2\times10^7$ cells/ml or more and less than $5\times10^7$ cells/ml.

D: A concentration of cells in a culture vessel is less than $2\times10^7$ cells/ml.

Judgment criteria for an amount of medium used are as follows.

A: A perfusion ratio is 1 or less.

B: A perfusion ratio is greater than 1 and 1.5 or less.

C: A perfusion ratio is greater than 1.5 and 2 or less.

D: A perfusion ratio is greater than 2.

Judgment criteria for aggregates in a culture vessel are as follows.

A: A sustainable culture period is 30 days or longer.

B: A sustainable culture period is 25 days to 29 days.

C: A sustainable culture period is 20 days to 24 days.

D: A sustainable culture period is 19 days or shorter.

Judgment criteria for a concentration of fine particles in a culture vessel are as follows.

A: A concentration of fine particles in a culture vessel is $5\times10^7$ particles/ml or less.

B: A concentration of fine particles in a culture vessel is more than $5\times10^7$ particles/ml and $10\times10^7$ particles/ml or less.

C: A concentration of fine particles in a culture vessel is more than $10\times10^7$ particles/ml and $40\times10^7$ particles/ml or less.

D: A concentration of fine particles in a culture vessel is more than $40\times10^7$ particles/ml.

Judgment criteria for a concentration of antibodies in a culture vessel are as follows.

A: A concentration of antibodies in a culture vessel is 1 g/l or less.

B: A concentration of antibodies in a culture vessel is more than 1 g/l and 2 g/l or less.

C: A concentration of antibodies in a culture vessel is more than 2 g/l and 4 g/l or less.

D: A concentration of antibodies in a culture vessel is more than 4 g/l.

Judgment criteria for filtration clogging of the first stage are as follows.

A: A period for which the first filter membrane can be used continuously is 30 days or longer.

B: A period for which the first filter membrane can be used continuously is 25 days to 29 days.

C: A period for which the first filter membrane can be used continuously is 20 days to 24 days.

D: A period for which the first filter membrane can be used continuously is 19 days or shorter.

Judgment criteria for filtration clogging of the second stage are as follows.

A: A period for which the second filter membrane can be used continuously is 30 days or longer.

B: A period for which the second filter membrane can be used continuously is 25 days to 29 days.

C: A period for which the second filter membrane can be used continuously is 20 days to 24 days.

D: A period for which the second filter membrane can be used continuously is 19 days or shorter.

Judgment criteria for an antibody recovery percentage are as follows.

A: An antibody recovery percentage is 90% or more.

B: An antibody recovery percentage is 80% or more and less than 90%.

C: An antibody recovery percentage is 60% or more and less than 80%.

D: An antibody recovery percentage is less than 60%.

Evaluation judgment criteria regarding a main peak percentage obtained by size exclusion chromatography are as follows.

A: A main peak percentage is 99% or more.

B: A main peak percentage is 97% or more.

C: A main peak percentage is 95% or more.

D: A main peak percentage is less than 95%.

Judgment criteria for comprehensive judgement are as follows.

A: There is no D and there are 7 or more A, and the judgment on the filtration clogging of the first stage is A.

B: There is no D and there is one or more A, and the criteria for the comprehensive judgement A are not satisfied.

C: There is no D and no A.

D: There is one or more D.

As shown in FIG. 6, Comparative Examples 1 to 4 are different from Example 1 to Example 21 in that an average hole diameter ratio (B/A) of an average hole diameter A of the first filter membrane 24 to an average hole diameter B of the second filter membrane 34 does not satisfy Equation (1). The comprehensive judgement in Comparative Examples 1 to 4 was all D based on the above-mentioned difference, whereas the comprehensive judgement in Examples 1 to 21 was any of A, B, and C. In other words, in Examples 1 to 21, antibody productivity could be improved while reducing an amount of medium used.

All of the documents, the patent applications, and the technical standards described in the present specification are incorporated into the present specification by reference, as if each of the documents, the patent applications, and the technical standards is specifically and independently described by reference.

EXPLANATION OF REFERENCES

10: culture vessel
11: stirring blade
20: first filter part
20*a*: inlet port
20*b*: outlet port
20*c*: exhaust port
21: vessel
22: supply side
23: permeation side
24: first filter membrane
30: second filter part
30*a*: inlet port
30*b*: outlet port
30*c*: exhaust port
31: vessel
32: supply side
33: permeation side
34: second filter membrane
40: recovery tank
41: tank
51, 52, 53, 53A, 53B, 54: flow path
55: backwash flow path
56, 57: recovery flow path
58: medium supply flow path
59: flow path
100, 100A, 100B: cell culture apparatus
200: twill woven mesh
201: weft yarn
202: warp yarn
C: cell
D: debris
FI1: first surface
FI2: second surface
OP, OP1, OP2: opening
P1 to P6: pump
V1 to V4: valve

What is claimed is:

1. A cell culture apparatus comprising:

a culture vessel that stores a cell suspension containing cells;

a first filter part that has a first filter membrane that performs membrane separation treatment on the cell suspension extracted from the culture vessel;

a first circulation flow path that allows components blocked by the first filter membrane to return to the culture vessel;

a second filter part that has a second filter membrane that performs membrane separation treatment on components of the cell suspension permeated through the first filter membrane;

a second circulation flow path that allows components permeated through the second filter membrane to return to the culture vessel; and a recovery flow path that recovers components blocked by the second filter membrane, wherein an average hole diameter of the first filter membrane is from 0.05 μm to 20 μm, and the second filter membrane is an ultrafiltration membrane having a molecular weight cut-off of 3 kDa or more.

2. The cell culture apparatus according to claim 1, wherein a system of the membrane separation treatment by the second filter membrane is a dead end system, and wherein the recovery flow path is provided between the first filter part and the second filter part.

3. The cell culture apparatus according to claim 1, wherein a system of the membrane separation treatment by the second filter membrane is a tangential flow system, and wherein the recovery flow path is connected to an outlet port of the second filter part by which components blocked by the second filter membrane flow outside the second filter part.

4. The cell culture apparatus according to claim 1, wherein the first filter membrane has an inlet-side opening which is formed on a first surface, and an outlet-side opening which is formed on a second surface opposite to the first surface and is communicated with the inlet-side opening, and the inlet-side opening and the outlet-side opening are disposed at positions mutually offset in a direction parallel to a membrane surface.

5. The cell culture apparatus according to claim 1, wherein the first filter membrane is a microfiltration membrane.

6. The cell culture apparatus according to claim 1, wherein a molecular weight cut-off of the second filter membrane is from 3 kDa to 100 kDa.

7. A cell culture method comprising:

a first membrane separation step of using a first filter membrane to perform membrane separation treatment on a cell suspension extracted from a culture vessel that stores the cell suspension containing cells, and allowing components blocked by the first filter membrane to return to the culture vessel;

a second membrane separation step of using a second filter membrane to perform membrane separation treatment on components permeated through the first filter membrane, and allowing components permeated through the second filter membrane to return to the culture vessel; and a recovery step of recovering components blocked by the second filter membrane via a recovery flow path, wherein an average hole diameter of the first filter membrane is from 0.05 μm to 20 μm, wherein the second filter membrane has a molecular weight cut-off of 3 kDa or more, and wherein $0<B/A\leq 0.5$ is satisfied in a case where an average hole diameter of the first filter membrane is A, and an average hole diameter of the second filter membrane is B.

8. The cell culture method according to claim 7, wherein $1.4<Y/X$ is satisfied in a case where a perfusion ratio, which is a ratio of an amount of components recovered in the recovery step per day to an amount of the cell suspension stored in the culture vessel, is X, and a circulation ratio, which is a ratio of an amount of components permeated through the first filter membrane in the first membrane separation step per day to the amount of the cell suspension stored in the culture vessel, is Y.

9. The cell culture method according to claim 8, wherein the perfusion ratio is 0.09 to 1.9.

10. The cell culture method according to claim 7, wherein a concentration of the cells contained in the cell suspension stored in the culture vessel is $2\times10^7$ cells/ml or more, and a concentration of fine particles that have a particle diameter of 2 μm to 4 μm and are contained in the cell suspension stored in the culture vessel is $40\times10^7$ particles/ml or less.

11. The cell culture method according to claim 7, wherein the cell is a cell that expresses an antibody, and a concentration of the cells contained in the cell suspension stored in the culture vessel is $2\times10^7$ cells/ml or more, and a concentration of the antibodies contained in the cell suspension stored in the culture vessel is 4 g/l or less.

12. The cell culture method according to claim 7, wherein a system of the membrane separation treatment by the first filter membrane is a tangential flow system.

13. The cell culture method according to claim 7, wherein, in the recovery step, the components blocked by the second filter membrane is continuously sent to the recovery flow path.

14. The cell culture method according to claim 7, wherein the cell is a cell that expresses an antibody, and wherein a permeate liquid permeated through the second filter membrane comprises a growth factor.

* * * * *